(12) United States Patent
Grubb et al.

(10) Patent No.: US 8,097,582 B2
(45) Date of Patent: Jan. 17, 2012

(54) PEPTIDE DERIVATIVES USEFUL AS ANTIMICROBIAL AGENTS AND FOR TREATING WOUNDS

(75) Inventors: Anders Grubb, Lund (SE); Aftab Jasir, Lund (SE); Claes Schalén, Lund (SE); Franciszek Kasprzykowski, Pruszcz Gdanski (PL); Regina Kasprzykowska, Pruszcz Gdanski (PL)

(73) Assignee: Neobiotics AB, Lund (SE)

( * ) Notice: Subject to any disclaimer, the term of this patent is extended or adjusted under 35 U.S.C. 154(b) by 463 days.

(21) Appl. No.: 12/300,033

(22) PCT Filed: May 4, 2007

(86) PCT No.: PCT/SE2007/000428
§ 371 (c)(1),
(2), (4) Date: Nov. 7, 2008

(87) PCT Pub. No.: WO2007/129952
PCT Pub. Date: Nov. 15, 2007

(65) Prior Publication Data
US 2009/0118198 A1    May 7, 2009

(30) Foreign Application Priority Data
May 9, 2006    (SE) .................................... 0601039

(51) Int. Cl.
*A61K 38/06* (2006.01)
*A61K 38/07* (2006.01)
*A61K 38/08* (2006.01)
*C07K 7/00* (2006.01)

(52) U.S. Cl. ........... 514/1.1; 514/2.4; 514/2.6; 530/329; 530/330; 530/331

(58) Field of Classification Search ........................ None
See application file for complete search history.

(56) References Cited

FOREIGN PATENT DOCUMENTS
WO    WO 00/35942    6/2000
WO    WO 2006/052201 A1 *    5/2006

OTHER PUBLICATIONS

Definition of derivative from http://cancerweb.ncl.ac.uk/omd/about.html, pp. 1-5. Accessed Jul. 7, 2005.*
Jasir et al. "New antimicrobial cystatin C-based peptide active against gram-positive bacterial pathogens, including methicillin-resistant *Staphylococcus aureus* and multiresistent coagulase-negative staphylococci." *APMIS*. 2003. pp. 1004-1010.
Jasir et al. "New antimicrobial peptide active against Gram-positive pathogens." *Indian J. Med. Res*. vol. 119. 2004. pp. 74-76.
Berezowska et al. "Highly potent fluorescent analogues of the opioid peptide [Dmt$^1$]DALDA." *Peptides*. vol. 24. 2003. pp. 1195-1200.
Panlilio et al. "Methicillin-Resistant *Staphylococcus aureus* in U.S. Hospitals, 1975-1991." *Infect Control Hosp. Epidemiol*. vol. 13. 1992. pp. 582-586.
Juszczyk et al. "Synthesis of orthogonally protected vicinal diamines with amnio acid-based skeleton." *Letters in Peptide Science*. vol. 9. 2002. pp. 187-192.
Kokotos et al. "A Convenient One-Pot Conversion of *N*-Protected Amino Acids and Peptides into Alcohols." *Synthesis Papers*. 1990. pp. 299-301.
Mattingly. "Mono-Protected Diamines. $N^\alpha$-*tert*-Butoxycarbonyl, α-Alkanediamine Hydrochlorides from Amino alcohols." *Sytnhesis Papers*. 1990. pp. 366-368.
O'Brien et al. "Inhibitors of Acyl-CoA:Cholesterol *O*-Acyl Transferase (ACAT) as Hypocholesterolemic Agents." *J. Med. Chem*. vol. 37. 1994. pp. 1810-1822.
Morris, Jr. et al. "Enterococci Resistant to Multiple Antimicrobial Agents, Including Vancomycin." *Annals of Internal Medicine*. vol. 123. No. 4. 1995. pp. 250-259.
Czaplewski et al. "Binding modes of a new epoxysuccinyl-peptide inhibitor of bysteine proteases. Where and how do cysteine proteases express their selectivity?" *Biochimica et Biophysica Acta*. vol. 1431. 1999. pp. 290-305.
Kasprzykowski et al. "Synthesis and antibacterial properties of peptydyl derivatives and cyclopeptides structurally based upon the inhibitory centre of human cystatin C." *APMIS*. vol. 108. 2000. pp. 473-481.

* cited by examiner

*Primary Examiner* — Julie Ha
(74) *Attorney, Agent, or Firm* — Merchant & Gould P.C.

(57) ABSTRACT

A compound having the general formula (I) $R_1$—NH—CH[$(CH_2)_n$—NH—C(NH)—$NH_2$]-CO—$R_2$-A-$R_4$; a pharmaceutical composition comprising the compound and use of the compound for the manufacturing of a medicament for the treatment of a disease such as a microbial disease and/or proliferation/stimulation of eukaryotic cells is described.

7 Claims, 1 Drawing Sheet

PEPTIDE DERIVATIVES USEFUL AS ANTIMICROBIAL AGENTS AND FOR TREATING WOUNDS

This application is a National Stage Application of PCT/SE2007/000428, filed 4 May 2007, which claims benefit of Ser. No. 0601039-1, filed 9 May 2006 in Sweden and Ser. No. 60/798,844, filed 9 May 2006 in the U.S. and which applications are incorporated herein by reference. To the extent appropriate, a claim of priority is made to each of the above disclosed applications.

FIELD OF INVENTION

The invention relates to a compound having the general formula (I)
$R_1$—NH—CH[$(CH_2)_n$—NH—C(NH)—$NH_2$]—CO—$R_2$-A-$R_4$, a pharmaceutical composition comprising said compound and use of said compound for the manufacturing of a medicament for the treatment of a disease such as a microbial disease or infection and/or proliferation/stimulation of eukaryotic cells.

BACKGROUND OF INVENTION

There is an increasing demand for the development of compounds having improved properties and which can be used against several different diseases, such as treatment of an infection or disease caused by a microorganism as well as for the stimulation of eukaryotic cells as well as for other purposes.

Concerning microbial diseases antibiotic research at the industrial level has been focused on the identification of more refined variants of already existing drugs and newer penicillins, cephalosporins, macrolides and fluoroquinolones were marketed. However, only one antibiotic based on a novel antimicrobial principle, linezolide, was created during three decades and resistance to the drug has already emerged during a few years of clinical use. Many antimicrobial peptides with new mechanisms of action have been reported; out of those active against bacteria most target the bacterial cell membrane by forming pores, for example antibiotics which are of microbial origin, and defensins, a large class of substances of mammalian origin. However, so far none of these substances has been developed into clinical use. Also, recent technical progress with combinatorial library technology has enabled the rapid design and testing of many substances intended for a defined target; again, in spite of considerable efforts no such compounds for medical use have been approved to date.

Resistance to old and newer antibiotics among bacterial pathogens is evolving rapidly, as exemplified by extended spectrum beta-lactamase (ESBL) and quinolone resistant gram-negatives, multi-resistant gonococci, methicillin resistant *Staphylococcus aureus* (MRSA), vancomycin resistant enterococci (VRE), penicillin non-susceptible pneumococci (PNSP) and macrolide resistant pneumococci and streptococci (Panlilo et al., Infect Control Hosp Epidemiol 1992; 13:582.586; Morris et al., Ann Intern Med 1995; 123:250-259). An overuse, or improper use, of antibiotics is probably of great importance for triggering and spread of bacterial resistance.

Economically, drug resistant pathogens represent a major burden for health-care systems. For example, postoperative and other nosocomial infections will prolong the need for hospital care and increase antibiotic drug expenses. At the community level, the current situation with PNSP has highlighted, that most existing antibiotics may fail against this pathogen, earlier known to be invariably susceptible to antibiotics.

In the case of viral diseases, few drugs for treatment are available in spite of intense research. For HIV, the situation has improved by the combined use of some drugs with different targets, delaying progression of the disease. Regarding herpes viruses, there is a need for improved drugs for both systemic and localised manifestations. Also for the SARS virus, effective treatment alternatives are lacking.

In the case of treatment of different kinds of wounds, such as wounds caused or complicated by viral, bacterial, protozoan and fungal infections, by insect bites, by direct lacerations, by insufficient blood supply, by irradiation as well as wounds caused by burns or pressure. The demand will even be higher in the near future due to the growing population of elderly people. If the wound is not properly cleaned and taken care of it often deteriorates and becomes permanent. Thus, a minor wound may be infected by bacteria and become a major clinical problem.

SUMMARY OF THE INVENTION

The invention relates to new invented compounds, which may be used for the manufacturing of medicaments which may be used to treat for example an infection and/or disease caused by or complicated by a microorganism as well as for the proliferation of eukaryotic cells or mixtures thereof, wherein the composition in an efficient and fast way, eliminates the microbes as well as stimulates the healing of a wound irrespective of its cause. However, the invented compounds may also be used for other purposes. Notably, the invented composition by its effect against microorganisms as well as aids in the proliferation of eukaryotic cells can be efficient in the treatment of infected wounds, wherein you may have one or more microbes such as a combination of bacteria and virus.

According to one aspect, the invention relates to a compound having the following formula (I)

$R_1$—NH—CH[$(CH_2)_n$—NH—C(NH)—$NH_2$]—CO—$R_2$-A-$R_4$     (I)

wherein
$R_1$ is H, Phe, or N-protected phenylalanine
or

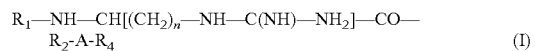

wherein
X is $CH_2$, NH, or O and m is 0-5 and Ar is an aryl or heteroaryl
and
n is 1-5
and
$R_2$ is an amino acid residue selected from the group consisting of Leu, Ile, Val, Gly, Phe, Thr, Pro and N-alkylated Gly
and
A is —NH—CH($R_3$)—$CH_2$—NH—
wherein $R_3$ is selected from the group consisting of hydrogen, sec-butyl, 1-hydroxyethyl, 4-hydroxybenzyl, alkyl, aryl, phenyl and derivatives thereof group
or
A is 2-aminomethylpyrrolidine, 6-phenetylpiperazin-2-one, or 3-isopropyl-6-phenetylpiperazin-2-one
and
$R_4$ is an acyl residue comprising an aryl or a heteroaryl
or
if A is 6-phenetylpiperazin-2-one or 3-isopropyl-6-phenetylpiperazin-2-one then $R_4$ is an acyl residue comprising an aryl, a heteroaryl, or $R_4$ is hydrogen.

In another aspect the invention relates to a pharmaceutical comprising the above defined compound and a pharmaceutically acceptable diluent, adjuvant, carrier, excipient or buffer.

In a further aspect the invention relates to the use of the above identified compound as well as the pharmaceutical composition as a medicament for the treatment of a disease.

In a final aspect the invention relates to the use of said compound or said pharmaceutical composition for the manufacturing of a medicament for the treatment of a microbial disease or infection and/or for the manufacturing of a medicament for the stimulation and/or proliferation of eukaryotic cells.

By the use of solely one compound or pharmaceutical composition it is possible for the first time to treat a mixture of disease or disorder as well as treat a mixture of diseases caused by different microbes as well as at the same time stimulate proliferation of cells and thereby for example reduce and heal a wound, such as a wound, e.g. caused by pressure, burn or other factors. Furthermore, the compound can effectively be used to reduce and/or eliminate combined infections, e.g. caused by both virus and bacteria or a mixture of bacteria and/or viruses.

DETAILED DESCRIPTION OF THE INVENTION

Definitions

Figure 1:
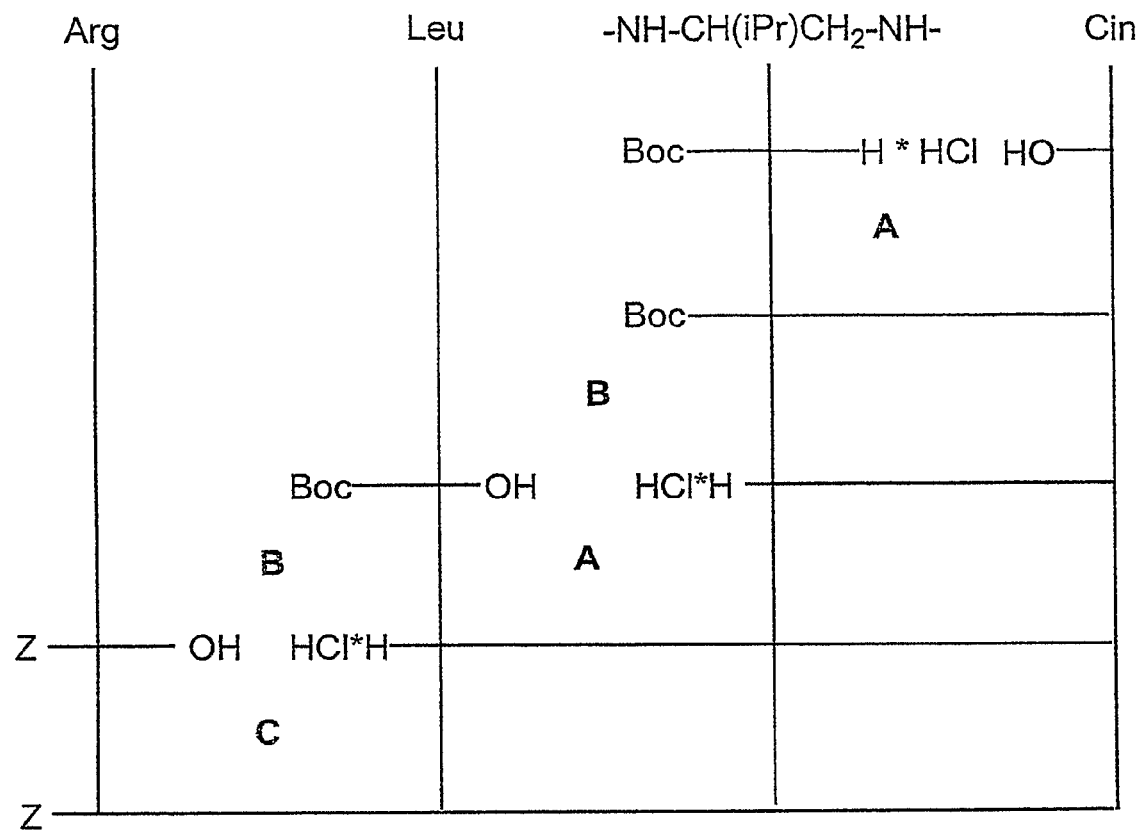
FIG. 1 shows an overview of the synthesis of the compounds.

In the context of the present application and invention the following definitions apply:

The term "resistant" is intended to mean resistant against at least one antimicrobial agent.

The term "multiresistant" is intended to mean at least resistant against two or more antimicrobial agents.

The term "compound"/"antimicrobial peptide" is intended to mean a compound/peptide which eliminates or inhibits the growth of bacteria, viruses, protozoans and/or fungi. The words "compound" and "peptide" are synonymously used within this particular application.

The term "proliferation" is intended to mean an increase in the cell number as a result of cell division. The proliferation may occur at a site, which has been harmed such as a wound. Examples of wounds are pressure and burn wounds as well as different kinds of wounds from external injury. The proliferation of cells may occur at any body site, including skin and internal surfaces.

The term "aryl" is intended to mean an unsaturated carbocycle, such as an aromatic cabocycle. Examples thereof comprise but are not limited to benzene, naphthalene, antracen, and phenanthrene.

The term "heteroaryl" is intended to mean an unsaturated ring or fused unsaturated rings, such as aromatic rings comprising at least one heteroatom, examples thereof comprises include, but are not limited to, pyridine, quinoline, isoquinoline, pyrimidine, quinazoline, thiophene, furan, indol, benzofuran, benzothiophene, imidazole, thiazole, oxazole, pyrazole, isothiazole, isooxazole, benzimidazole, benzoxazole, benzthiazole, purine, triazole, and tetrazole.

The term "N-protected" is intended to mean that the amino group of the amino acid is substituted to modify the reactivity of the nitrogen. There are numbers of ways (see eg. "Protective Groups in Organic Synthesis, 3:rd ed." eds. Theodora W. Greene and Peter G. M. Wuts; John Wiley and Sons, Inc. New York) to protect nitrogen, e.g. acetylation.

The term "derivative thereof" is intended to mean peptides derived from the compound (I) in which one or more residues of the side chain is transferred from the alpha carbon to the nitrogen of that particular residue (peptides). Additionally, consisting N-methyl amino acid or reduced peptide bond or peptide bond may be replaced by double carbon-carbon bond, hydroxymethylene or carbonylmethylene moiety, or combinations thereof.

In the present context, amino acid names and atom names are used as defined by the Protein Data Bank (PDB), which is based on the IUPAC nomenclature (IUPAC Nomenclature and Symbolism for Amino Acids and Peptides (residue names, atom names etc.), Eur J. Biochem., 138, 9-37 (1984) together with their corrections in Eur J. Biochem., 152, 1 (1985). The term "amino acid" is intended to indicate an amino acid from the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), phenylglycine (Phg), glutamine (Gln or Q), arginine (Arg or R), serine (Ser or S), threonine (Thr or T), valine (Val or V), tryptophan (Tip or W) and tyrosine (Tyr or Y), or derivatives thereof.

Compound

The invention relates to a compound having the following formula (I)

$$R_1-NH-CH[(CH_2)_n-NH-C(NH)-NH_2]-CO-$$
$$R_2-A-R_4 \quad (I)$$

wherein
$R_1$ is H, Phe, or N-protected phenylalanine
or
$R_1$ is Ar—$(CH_2)_m$—X—CO—
wherein
X is $CH_2$, NH, or O and m is 0-5 and Ar is an aryl or heteroaryl
and
n is 1-5
and
$R_2$ is an amino acid residue selected from the group consisting of Leu, Ile, Val, Gly, Phe, Thr, Pro and N-alkylated Gly
and
A is —NH—CH($R_3$)—$CH_2$—NH—
wherein $R_3$ is selected from the group consisting of hydrogen, sec-butyl, 1-hydroxyethyl, 4-hydroxybenzyl, alkyl, aryl, phenyl and derivatives thereof
or
A is 2-aminomethylpyrrolidine, 6-phenetylpiperazin-2-one, or 3-isopropyl-6-phenetylpiperazin-2-one
and
$R_4$ is an acyl residue comprising an aryl or a heteroaryl
or
if A is 6-phenetylpiperazin-2-one or 3-isopropyl-6-phenetylpiperazin-2-one then $R_4$ is an acyl residue comprising an aryl, a heteroaryl, or $R_4$ is hydrogen
for the manufacturing of a medicament for the proliferation of cells.

Additionally, any kind of modification may be introduced as long as the above, defined general structure is maintained.

The chiral residues, i.e., the amino acid residues within the compound may be, independent of each other, in the D or L-form without influencing the activity of the compound. The same applies for diastereomeric as well as enantiomeric forms.

Additionally, $R_4$ may be selected from the group consisting of cinnamoyl, acetyl-L-phenylalanine, acetyl-D-phenylalanine and —CO—$(CH_2)_p$-Ph wherein p=2-7 or derivatives thereof and $R_3$ may be iso-propyl and $R_2$ may be Leu. The number of n may vary between 1-5, such as be 2, 3 or 4 and the numbers of m may vary between 0-5, such as being 1, 2, 3 or 4. In one example $R_1$ is Ar—$(CH_2)_m$—X—CO—, where X is CH$_2$O, m is 1 and Ar is phenyl and in another example compound is (2S)-2-[(N$^a$-Benzyloxycarbonyl-arginyl-leucyl)-amino]-1-trans-cinnamoylamino-3-methylbutane.

The compound may be a cyclic compound wherein R$_1$ and R$_4$ are linked with Arg-Leu-Val or Orn-Leu-Val bridges.

Additionally, minor modification of the compound of the invention may be performed as long as its activity is retained, such as modifications of the bonds between the residues derived from amino acids.

Examples of compounds may be found below.

R$_4$
trans-cinnamoyl
Hydrogen-
L-2-bromo-3-phenylpropionyl
D-2-bromo-3-phenylpropionyl
L-2-hydroxy-3-phenylpropionyl
D-2-hydroxy-3-phenylpropionyl

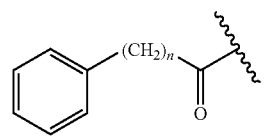

n = 1
n = 2
n = 3-7 trans-3-benzylacroyl
(2S,3S)-3-phenylglycidyl
(2S,3R)-3-phenylglycidyl
(2S,3S)-3-benzoylglycidyl
trans-3-benzylsulphonylacroyl
Phenylpropiolyl
(E)-2-bromocinnamoyl
Chloroacetyl
2-(4-pyridyl)acroyl
acetyl-L-phenylalanoyl
acetyl-D-phenylalanoyl
5-phenylpenta-2,4-dienoyl
4-phenylcinnamoyl
R$_1$=
hydrogen-
Acetyl
Phenylacetyl
3-phenylpropionyl
4-phenylbutyryl
Benzyloxycarbonyl Said composition may for example be used to combat microorganisms, alone or in combinations, such as combating a mixture of viruses, bacteria, protozoans and fungus as well as a mixture of bacteria and/or virus and/or protozoans and/or fungus. Examples of bacteria are gram positive bacteria such as Staphylococci, such as *S. aureus* and *S. epidermidis*, coagulase negative staphylococci (CNS), β-hemolytic streptococci groups A, B, C and G (GAS, GBS, GCS and GGS), pneumococci, groups A, B, C and G streptococci and *Listeria* spp. Pathogenic viruses such as picorna virus in particular enterovirus, comprising poliovirus, coxsackieviruses groups A and B and Echoviruses and also Herpesviridae, in particular simplex virus, comprising Herpes Simplex type 1 and 2. Other examples of viruses are hepatitis A, B and C. Examples of fungus includes *Candida* ssp., in particular *C albicans*, dermatophytes and moulds. Other examples are SARS, HIV, H5N1 as well as adeno-, coxsackie- and rhinoviruses. Examples of fungus are *Candia* spp, such as *C. grabrata*, *C. dermatophytes* as well as moulds.

The in vitro antibacterial activity of drugs is commonly estimated by testing their minimal inhibitory (MIC) and bactericidal (MBC) concentrations. The MICs of some of the compounds for both *S. aureus* and GAS were found to be approximately 16 mg/L, thus somewhat higher than for clinically effective drugs; however, these tests were performed in growth media without DMSO, implying solubility problems, and true MIC values might therefore be considerably lower. Furthermore, the finding that MIC and MBC were similar for tested species indicated that the antibacterial action of the defined compounds shown in the figures is bactericidal rather than bacteriostatic.

Experiments in cell culture have shown that the compounds shown in the figures are active against viruses, such as polio and Herpes simplex, representing RNA and DNA viruses, respectively. No cytopathic effects for the cell line used were recorded indicating that the compounds may not be toxic for eukaryotic cells. Additionally, the compounds may be used to combat other viruses such as SARS, HIV, H5N1, hepatitis A,B and C and adeno-, coxsackie- or rhinoviruses, and fungi, i.e., *Candida* spp., such as *C. albicans*.

The compounds shown in the figures are novel, short-chain peptidomimetics derivatives. All display antibacterial activity against major human pathogens, such as *S. aureus*, CNS, groups A, B, C and G streptococci, and *L. monocytogenes*. They have low or no activity against gram-negative bacteria or α-haemolytic Streptococci. Such a property, from a clinical point of view, would be advantageous since most existing antibiotics exhibit harmful side-effects due to profound disturbances of the normal throat or gut flora. Notably, attempts in vitro to create bacterial mutants resistant to the compounds, have failed so far. Accordingly the compounds shows effects against different viruses as well as they stimulate the proliferation of eukaryotic cells, which means that the compounds may effectively be used to combat as well as treat certain diseases wherein there is a need of stimulating the eukaryotic cells to proliferate and/or inhibiting the growth of microorganisms such as those mentioned above alone or in combination.

The compounds may be produced using conventional methods well known for a person skilled in the art. Possible methods can be found in the examples.

The above, mentioned compositions are suitable for medical use, and there are several kinds of human infection/disease or disorders with current treatment problems that may potentially be treated/cured. Depending on the causative microbe(s) and/or for example wounds the compounds may be used alone or in combination with other antimicrobial agents to combat bacterial, viral, fungal and/or protozoan infection(-s) or other wound healing components.

Among bacterial diseases, systemic and local infections with MRSA (methicillin resistant *S. aureus*), with extensive resistance to antibiotics and increasing prevalence worldwide, may be the most important category. For the same reason, treatment of opportunistic infections caused by coagulase negative streptococci (CNS) often nosocomial and foreign device related, may be suitable for treatment with the above mentioned compounds, such as those shown in the figures. For pathogenic streptococci, antibiotic resistance is of current concern; however, invasive infections caused by streptococci are often life threatening in spite of antibiotic treatment, and successful treatment might require drugs with targets distinct from these of hitherto available antibacterial drugs. Additionally, common throat and skin infections caused by streptococci, often relapsing following antibiotic treatment, may be suitable for future treatment with the above, mentioned compounds.

The compounds according to the invention may also be used in the treatment of viral infections or diseases, such as oral, genital or systemic, caused by virus, such as herpes viruses.

The invented compositions may also be used for the treatment of any disease or disorder in which there is a need of proliferation of eukaryotic cells. Examples are different kinds of wounds, caused by viral, bacterial, protozoan and fungal infections, by insect bites, by direct lacerations, by insufficient blood supply or wounds caused by pressure or burn.

The differences between some of the compounds mentioned above are the following;

| Compound | Figure | $R_1$ | $R_2$ | $R_3$ | $R_4$ |
|---|---|---|---|---|---|
| Cp 1 | A20 | Benzyloxy-carbonyl | Leu | Isopropyl | trans-cinnamoyl |
| [AcPhe$^5$]Cp1 | A132 | Benzyloxy-carbonyl | Leu | Isopropyl | N-acetyl-phenylalanoyl |
| [Phe$^4$]Cp1 | A83 | Benzyloxy-carbonyl | Leu | benzyl | trans-cinnamoyl |
| [Leu$^4$]Cp1 | A84 | Benzyloxy-carbonyl | Leu | isobutyl | trans-cinnamoyl |
| [Gly$^3$]Cp1 | A92 | Benzyloxy-carbonyl | Gly | isopropyl | trans-cinnamoyl |
| [Ac-D-Phe$^5$]Cp1 | A133 | Benzyloxy-carbonyl | Leu | isopropyl | N-acetyl-D-phenylalanoyl |

"Pharmaceutically acceptable" means a diluent, buffer, carrier or excipient that at the dosage and concentrations employed does not cause any unwanted clinical effects. Such pharmaceutically acceptable buffers, carriers or excipients are well-known in the art; see Remington's Pharmaceutical Sciences, 18th edition, A. R Gennaro, Ed., Mack Publishing Company (1990) and Handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES. The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition.

The excipient may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The composition may be admixed with adjuvants such as lactose, sucrose, starch powder, cellulose esters of alkanoic acids, stearic acid, talc, magnesium stearate, magnesium oxide, sodium and calcium salts of phosphoric or sulphuric acid, gelatin, sodium alginate, polyvinyl-pyrrolidine, and/or polyvinyl alcohol, and tableted or encapsulated for conventional administration.

Alternatively, the compounds may be dissolved in saline, water, polyethylene glycol, propylene glycol, ethanol, oils, tragacanth gum, and/or various buffers. Other adjuvants and modes of administration are well known in the pharmaceutical art. The carrier or diluent may include time delay material, such as glyceryl monostearate or glyceryl distearate, alone or with a wax, or other materials well known in the art.

The compositions may be subjected to conventional pharmaceutical operations such as sterilisation and/or may contain conventional adjuvants, such as preservatives, stabilisers, wetting agents, emulsifiers, buffers, fillers, etc., e.g. as disclosed elsewhere herein.

The composition according to the invention may be administered locally or systemically, such as topically, intravenously, orally, parenterally or as implant, and even rectal use is possible. Suitable solid or liquid pharmaceutical preparation forms are, for example, granules, powders, tablets, coated tablets, (micro)capsules, suppositories, syrups, emulsions, gels, ointments, suspensions, creams, aerosols, drops or injectable solutions in ampoule form and also preparations with protracted release of active compounds, in which preparations, excipients, diluents, adjuvants or carriers are customarily used as described above. The composition may also be provided in bandages or plasters or the like.

The composition will be administered to a patient in a pharmaceutically effective dose. By "pharmaceutically effective dose" is meant a dose that is sufficient to produce the desired effects in relation to the condition for which it is administered. The exact dose is dependent on the activity of the compounds, manner of administration, nature and severity of the disorder, age and body weight of the patient and adjustment of dosage may thus be needed. The administration of the dose can be carried out both by single administration in the form of an individual dose unit or several smaller dose units, but also by multiple administrations of subdivided doses at specific intervals.

The composition according to the invention may be administered alone or in combination with other therapeutic agents, such as antibiotics or antiseptic agents. Examples are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, chlorhexidine, polyhexanide and other biguanides, acetic acid, and hydrogen peroxide. These agents may be incorporated as part of the same composition or may be administered separately.

Finally, the invention relates to a method of triggering proliferation of eukaryotic cells in an animal or a human being having one or more wounds.

Following examples are intended to illustrate, but not to limit, the invention with regard to shape or form, either explicitly or implicitly.

EXAMPLES

Example 1

Synthesis of the Different Compounds (General Scheme See FIG. 1)

Procedure A—Coupling.

10 mmol of the amine component (hydrochloride) was dissolved in 50 ml of dimethylformamide (DMF). Next, 1.4 ml (10 mmol) of triethylamine, 12 mmol of carboxy-component and 18 mmol of 1-hydroxybenzotraizole (HOBt) was added. The mixture was cooled on ice bath and 12 mmol of dicyclohexylcarcodiimide (DCC) was added in small portions during 30 min., with vigorous stirring. The reaction mixture was stirred on ice bath 1 hour, and then left at room temperature overnight. The precipitated dicycolhexylurea (DCU) was filtered off and washed with DMF, and the combined filtrates were evaporated to dryness under reduced pressure. The solid residue was dissolved in ethyl acetate, and the resulting solution was washed with water (1×100 ml), ice-cold 1N HCl (3×50 ml), water (1×100 ml) saturated NaHCO$_3$ (3×50 ml) and finally with water (3×70 ml). The organic layer was dried over anhydrous MgSO$_4$. The drying agent was filtered off, pre-washed with ethyl acetate and the combined filtrates were evaporated to dryness under reduced pressure. The solid residue was dissolved in hot toluene and precipitated with petroleum ether. Yield approximately 90%.

Procedure B—Deprotection.

The Boc-protected compound (10 mmol) was dissolved in 50 ml 4 N solution of (anhydrous) HCl in dioxane. The solution was stirred during 30 min. at room temperature, and then evaporated under reduced pressure to dryness. The solid residue was triturated with anhydrous diethyl ether. The solid residue was filtered off, washed with anhydrous diethyl ether and dried.

Procedure C—Coupling with Z-Arg-OH

The amino-component (10 mmol) was dissolved in DMF (70 ml), and 4,59 g (30 mmol monohydrate) HOBT was added. To the solution was diisopropyletylamine (DIPEA) added dropwise, until the pH of the mixture, controlled with wet indicator paper reached 7-8. Next, the N-benzyloxycarbonyl-arginine hydrochloride (5.17 g, 15 mmol) was added and the solution was cooled on ice bath. N,N'-Dicyclohexylcarbodiimide (3.09 g, 15 mmol) was added in small portions during 1 h. and after additional 1 h of stirring, the reaction mixture was left in a cold room overnight (approximately 4° C.). The precipitated DCU was filtered off and washed with a small volume of DMF and the combined filtrates were evaporated under reduced pressure. From the resulting mixture A20 (or its analogues) was isolated using chromatography techniques.

Isolation of A20 or its Analogue, Hereinafter Only Named A20

Small amounts (100-200 mg) of A20 may be isolated using SPE technique on RP-C-18 stationary phase, or directly purified on RP-HPLC column (20×250 mm) filled with Kromasil-100-5-C8. The mobile phases contained triethylamine phosphate buffer (TEAP, pH=3, 0.05-0.2 M). Fractions containing A20 were combined and the acetonitrile was removed by evaporation under reduced pressure. The resulting solution was pumped through the Kromasil column equilibrated with 5% MeCN-0.1% trifluoroacetic acid (TFA). The column buffer was washed out with 5% MeCN-0.1% TFA, next A20 was eluted using a gradient of 5-50% MeCN containing 0.1% TFA during 1 hour. Fractions containing A20 were concentrated and lyophilized. The substance obtained by this manner substance contains TFA as a counter ion.

Alternatively, a procedure for isolation of A20 using SP-Sepharose FF, wherein large excess of the ion exchanger (100× molar excess or more) was used. The Sepharose column was equilibrated with 0.005 M sodium acetate-acetic acid buffer (pH=4.75) in 50% MeOH. The sample containing A20 was injected into the column and unbounded substances were eluted with 50% MeOH containing 0.005 M acetate buffer. Next, the A20 was eluted with a gradient of KCl (0-0.2 M). Due to weak solubility of A20 in the presence of salts, the resulting peak was very broad, especially when the injected amount of A20 was large. A narrower peak was obtained, when ammonium acetate was used in the place of potassium chloride. The fractions containing A20 were combined and evaporated to dryness. The Cystapep was extracted with anhydrous MeOH and purified by RP-HPLC. When ammonium acetate was used, the salt was removed by lyophilization.

The final purification of A20 was performed using a Kromasil column, using approximately 29% MeCN-0.1M TEAP, pH=3 as a mobile phase or ca. 29% iPrOH-0.2 M ammonium acetate-acetic acid buffer (pH=5) as a mobile phase. In this last case, the additional desalting step is not necessary, because the ammonium acetate may be removed by lyophilization, Synthesis of Mono-Boc-Protected Diamines Desired Boc-protected alcohols may be obtained from proper Boc amino acid, in accordance with the literature procedures [1,2]. Obtained Boc-aminoalcohols were converted into mono-Boc-protected diamines in accordance with literature procedures [3,4]. The best results were obtained when a combination of these two procedures was used. The mesyl-derivative of alcohol was obtained in accordance to the procedure of [4]. The azide was obtained generally in accordance with the same procedure, but in the presence of tetrabutylammonium bromide, like in the procedure of [3]. The inorganic salts were filtered off, washed with dimethylformamide and the combined filtrates were evaporated under reduced pressure. The oily residue was dissolved in diethyl ether and treated in this same manner as described in [3]. The reduction of azide to amine was carried out as described in [3] In specific embodiments the mono-Boc-protected diamine is acylated with Z-Phe (D or L-isomer), next the Z (benzyloxycarbonyl) protective group is removed by hydrogenolysis, and the resulting compound is acetylated with acetic anhydride.

References

1. Kokotos G. *A convenient one-pot conversion of N,N-protected amino acids and peptides into alcohols.* Synthesis 1990: 299-30.
2. Juszczyk P. Lankiewicz L. Kolodziejczyk A. *Synthesis of othogonally protected vicinal diamines with amino acid-based skeleton.* Lett. Pep. Sci. 2002; 9:187-92
3. Mattingly P. G. *Mono-protected diamines. N$^\alpha$-tert-butoxycarbonyl-α, ω-alkanediaminehydrochlorides from amino alcohols.* Synthesis 1990: 366-8.
4. O'Brien P. M. Sliskovic D. R. Blankley J. Roth B. D. Wilsom M. W. Hamelehle K. L. Krause B. R. Stanfield R. L. *Inhibitors of acyl-Co-A transferase (ACAT) as hypocholesterolemic agents. Incorporation of amide or amine functionalities into a series of disubstituted ureas and carbamates. Effect of ACAT inhibition in vitro and efficacy in vivo.* J. Med. Chem. 1994; 37:1810-22.

Example 2

Synthesis of 4A20

The (2S)-1-amino-2-tert-butyloxycarbonylamino-3-methylbutane hydrochloride was obtained from tert-butyloxycarbonyl-L-valine in accordance with the literature procedures [1,2]. m.p. 175-176° C.; $[\alpha]_D^{22}$=+5|(c=1, ethanol).

Elemental analysis:
calculated: 50.31% C, 9.71% H, 11.73% N;
found: 49.65% C, 9.74% H, 11.76% N;

IR (KBr): 3375 (NH, urethane), 2876 ($NH_3^+$, amine) 1683, (C=O urethane), 1165 (C—O, urethane) [$cm^{-1}$]

Synthesis of (2S)-2-Tert-Butyloxycarbonylamino-1-trans-cinnamoylamino-3-methylbutane The solution of (2S)-1-amino-2-tert-bytyloxycarbonylamino-3-methylbutane hydrochloride (2.38 g 10 mmol), triethylamine (1.7 ml, 12 mmol), HOBt (2.70 g. 20 mmol) and trans-cinnamic acid (1.77 g, 12 mmol) in 50 ml of tetrahydrofurane (THF) was cooled in an ice bath, and DCC (1.54 g, 7.5 mmol) was added in small portions, during 30 min. The stirring was continued for 1 hour, and next the reaction mixture was left in room temperature overnight. The precipitate DCU was filtered off and washed with two portions of THF (15 ml of each).

Combined filtrates were evaporated under reduced pressure and the solid residue was dissolved in 150 ml of ethyl acetate. The solution obtained was washed with ice-cold 1M hydrochloric acid (3×50 ml), water (100 ml), a saturated water solution of sodium bicarbonate (3×50 ml) and saline (2×50 ml). The organic layer was dried over anhydrous magnesium sulphate and evaporated to dryness. The resulting solid was crystallized from toluene-petroleum ether, yielding 2.95 g (88.7%) of (2S)-2-tert-butyloxycarbonylamino-1-trans cinnamoylamino-3-methylbutane, m.p.=149-151° C.; $[\alpha]_D^{20}$=–0.91° C. (c=1, methanol).

Elemental analysis:
calculated: 68.65% C, 8.49% H, 8.49% N;
found: 68.69% C, 8.73% H, 9.01% N.
IR (KBr) 3359 (NH, urethane), 3326 (N—H, amide), 1688 (C=O, urethane), 1173 (C—O, urethane), 964 (=C—H, cinnamoyl), 764 (CH, phenyl), 723 (CH phenyl) [$cm^{-1}$].

Synthesis of (2S)-2-[$N^\alpha$-tert-Butyloxycarbonyl-leucyl)-amino]-1-trans-cinnamoylamino-3-methylbutane (2S)-2-tert-Butyloxycarbonylamino-1-trans-cinnamoylamino-3-methylbutane (2.5 g. 7.5 mmol) was dissolved in 40 ml of 4N hydrochloride in anhydrous dioxane. The reaction mixture was stirred during 30 min. at room temperature and evaporated under reduced pressure. The residue was triturated with 50 ml of anhydrous diethyl ether, filtered under reduced pressure, washed twice with diethyl ether (2×20 ml) and dried in a vacuum desiccator over potassium hydroxide. The resulting (2S)-2-amino-1-cinnamoylamino-3-methylbutane hydrochloride (1.78 g, 7.35 mmol) was dissolved in 50 ml of THF and triethylamine (1 ml, 7.5 mmol), HOBt (2.00 g, 15 mmol) and Boc-L-leucine monohydrate (1.87 g, 7.5 mmol) were added to the solution. The mixture was cooled on ice bath and DCC (1.54 g, 7.5 mmol) was added in small portions, during 30 min., with vigorous stirring. The mixture was stirred in an ice bath for one additional h and left at room temperature overnight. The precipitated DCU was filtered off, washed with THF (2×15 ml) and the combined filtrates were evaporated under reduced pressure. The solid residue was dissolved in 100 ml of ethyl acetate and the solution was washed with ice-cold 1M hydrochloric acid (3×50 ml), water (100 ml), a saturated aqueous solution of sodium bicarbonate (3×50 ml) and saline (100 ml). The organic layer was dried over anhydrous magnesium sulphate and evaporated to dryness. The residue was dissolved in hot toluene and precipitated with petroleum ether, yielding 2.97 g (88.9%) of (2S)-2-[(N-tert-butyloxycarbonyl-leucyl)-amino]-1-trans-cinnamoylamino-3-methylbutane.

Synthesis of (2S)-2-[($N^\alpha$-Benzyloxycarbonyl-arginyl-leucyl)-amino]-1-trans-cinnamoylamino-3-methylbutane (2S)-2-[(N-tert-Butyloxycarbonyl-leucyl)-amino]-1-trans-cinnamoylamino-3-methylbutane (0.668 g, 1.5 mmol) was dissolved in 25 ml of 4 N solution of anhydrous hydrochloride in dioxane. The reaction mixture was stirred during 30 min. at room temperature and then evaporated to dryness under reduced pressure. The residual oil was triturated with anhydrous diethyl ether (50 ml). The obtained solid was filtered off under reduced pressure, washed with anhydrous diethyl ether (3×20 ml) and dried under vacuum over potassium hydroxide. The resulted (2S)-2-(leucylamino)-1-(trans-cinnamoylamino)-3-methylbutane hydrochloride (0.545 g, 1.43 mmol) was dissolved in 10 ml of DMF. Next, HOBt, (0.405 g, 3 mmol) was added and pH of the mixture was adjusted to 7.5 with triethylamine (controlled with wet indicator paper), and then the $N^\alpha$-benzyloxycarbonyl-arginine hydrochloride (1.034 g, 3 mmol) was added. The reaction mixture was cooled on ice bath, and then the DCC (0.619 g, 3 mmol) of was added in small portions during 30 min. The mixture was stirred during additional 1 hour on ice bath and overnight at room temperature. The precipitated DCU was filtered off and washed with 20 ml of DMF. Combined filtrates were evaporated and the resulted residue was dissolved in 200 ml of 50% aqueous ethanol acidified with 20 ml of acetic acid. The solution was filtered and pumped through chromatographic column (50×200 mm) filled with S-Sepharose FF, equilibrated with 0.001 M sodium acetate-acetic acid buffer (pH=4.75) in 50% ethanol. The column was washed with an additional 750 ml of 0.001 M sodium acetate-acetic acid buffer in 50% ethanol, and the product was eluted with the linear gradient of potassium chloride (from 0 to 0.2 M of KCl in total amount of 2 l of eluent. Flow rate-20 ml/min). Fractions containing A20 were collected, evaporated to dryness and extracted with 50 ml of methanol. The insoluble inorganic salts were filtered off, washed with 20 ml of methanol and combined filtrates evaporated to dryness. The residue (1.1 g) was dissolved in 30 ml of 29% (v/v) isopropanol-water solution containing 0.2 M of TEAP buffer (pH=2.8). Half of the solution was injected on the RP-HPLC column (50×250 mm, filled with Kromasil Kr-100-7-C-8), equilibrated with 29% (v/v) isopropanol-water solution containing 0.2 M of TEAP buffer and eluted with this same solvent system (isocratic elution), at flow rate 25 ml/min. The eluate was monitored using UV detector at λ=226 nm. Fractions containing pure A20 were collected, evaporated to half of volume and pumped through the same column equilibrated with 0.1% TFA in 5% solution of isopropanol (iPrOH) in water (v/v/v) (5% iPrOH, 0.1% TFA/$H_2O$). The column was washed out with additional 1.5 l of 0.1% TFA in 5% solution of iPrOH in water, and next, the A20 was eluted in gradient from 5% iPrOH, 0.1% TFA/$H_2O$ to 50% iPrOH, 0.1% TFA/$H_2O$ during 90 min. Flow rate 25 ml/min, monitoring of the eluate as described above. Fractions containing A20 were collected, concentrated under reduced pressure and lyophilized. The second half of the crude A20 solution was worked up in the same manner. Yield-0.682 g (60.6%) of A20 as trifluoroacetate salt.

=–16.9° (c=1, methanol);
MS (MALDI-TOF): m/z=636.4 $[M+H]^+$
Elemental analysis:
calculated (for $C_{34}H_{49}N_7O_5$.TFA.$H_2O$): 56.31% C, 6.83% H, 12.77% N;
found: 56.70% C, 6.70% H, 12.45% N.
IR (KBr) [$cm^{-1}$]: 3299 (NH), 1655 (C=O, urethane) 1642 (C=O amide), 1181 (C—O urethane), 766 (CH phenyl), 721 (CH phenyl)

Test of Concentration of the Compounds

Different solutions of the different compounds shown in the figures were centrifuged at 300 g for 15 min. Aliquots of the clear supernatants were used for quantitative amino acid analysis after evaporation followed by hydrolysis at 110° C. for 20 h in 6M HCl. An automated system, Beckman High Performance Analyzer, model 6300, was used for the amino acid analysis. The amounts of amino acids released were then used to calculate the concentration of the different compounds from their known structures.

Test of Concentration of the Compounds

Different solutions of the different compounds A01-A133 mentioned above were centrifuged at 300 g for 15 min. Aliquots of the clear supernatants were used for quantitative amino acid analysis after evaporation followed by hydrolysis at 110° C. for 20 h in 6M HCl. An automated system, Beckman High Performance Analyzer, model 6300, was used for the amino acid analysis. The amounts of amino acids released were then used to calculate the concentration of the different compounds from their known structures.

Example 3

Antibacterial Analysis

Clinical isolates and reference strains including *Streptococcus pyogenes* type Ml, *Streptococcus agalactiae* (NCTC 8181), *Streptococcus equisimilis* (ATCC 12388), *Streptococcus pneumoniae* (ATCC49619), *Staphylococcus aureus* (ATCC 29213), *Staphylococcus epidermidis* (ATCC 14990) were tested. The clinical isolates were isolated by the University Hospital, Lund, Sweden and included a variable numbers of *S. aureus* including MRSA, CNS, groups A, B, C and G streptococci (GAS; GBS; GCS; GGS, respectively), *Staphylococcus aureus*, coagulase negative staphylococci (CNS), *Enterococcus faecium*, viridans streptococci, *Streptococcus pneumoniae*, *Listeria monocytogenes*, *Moraxella catarrhalis*, *Haemophilis influenaae*, *E. coli*, *Klebsiella pneumoniae* and *Pseudomonas aeruginosa*.

The antibacterial activity of the different compounds A01-A133 were tested by agar well diffusion. Strains were grown aerobically at 37° C. for 18 hours on blood agar base (LabM) with 4% defibrinated horse blood. However, *Haemophilus influenzae* was grown on Blood agar base No 2 (Oxoid) containing 7% haematized horse blood in 5% $CO_2$ atmosphere. From each strain 5-10 colonies were suspended in 10 ml saline to an optical density of approximately 0.5 McFarlands units, vortexed rigorously and inoculated onto IsoSentitest agar (Oxoid), or onto haematin agar as indicated above, using cotton-tipped swab. The thickness of the solid media was 5 mm. Wells of 5 mm diameter were punched in the agar and 40 ul of a solution of each of the tested compounds (1 mg/ml) in DMSO was applied to each hole. After prediffusion at room temperature for 0.5 h the plates were incubated at 37° C. for 14 h aerobically or in 5% $CO_2$ atmosphere as described above.

MIC/MBC determinations were performed by broth dilution according to established procedures, well known for a person skilled in the art.

Example 4

Antiviral Analysis

Test substance;
Acyclovir 1.0 mM
The compounds A01-A133 0.4 mM in 1% DMSO
DMSO 1%
Inhibition Analysis GMK (Green Monkey Kidney) AH 1 cells were grown in 24 well plates with 1 ml Minimum Essential Medium (MEM) cell culture medium containing glutamax (MEM-glutamax), 10% fetal calf serum and gentamicin (final conc 50 mg/L). When cells had reached a concentration of $5 \times 10^5$ cells/well, the cell culture medium was removed and the cells incubated with HSV-1 F (Herpes Simplex Virus) (Ejercito et al., J Gen Virol 1968; 2:357-364) at a concentration of 10 PFU (plaque forming units)/cell or with poliovirus type 1 at a concentration of 1 PFU/cell. After 2 hours of incubation at 37° C. the virus containing medium was removed and the cells washed 4 times in PBS. Then 0.5 ml MEM-glutamax containing gentamicin (as above, conc 50 mg/L) with or without test substance was added. The cells were incubated for 48 hours at 37° C. in a $CO_2$ incubator and then frozen at −30° C.

Plaque Counting Test

Cell culture medium with the frozen cells obtained from the inhibition test was thawn and diluted in 7 steps from 1 to $10^{-7}$. The plaque titration was performed using GMK AH 1 cells in MEM-glutamax with gentamicin. The cells were washed three times with PBS and incubated in petri plates with different dilutions of the virus containing cell culture medium obtained in the inhibition test. The cells were incubated for 1 hour at 37° C. The medium was removed by washing the cells once with PBS. Then an agar (Bacto-Agar) overlay was added and the plates were incubated at 37° C. for 3 days. The plaques were counted (Johansson et al., Intervirology 1988; 29:334-338).

The different compounds showed different activity against the viruses (data not shown).

Example 5

Antifungal activity

The minimal inhibitory concentration (MIC) was determined using a method with Sabouraud broth (Becton Dickinson) and an initial inoculum $10^3$-$10^4$ cfu/ml. Polypropylene 96-well plates (Nunc) were incubated at 25° C. for 48 h (for *Candida albicans* ATCC 10231) or 7 days (for *Aspergillus niger* ATCC 16404). The MIC was taken as the lowest drug concentration at which noticeable growth was inhibited. The results showed that the different compounds showed different activity against the fungus (data not shown).

Example 6

A20, A83 and A84 were added to a softening cream and 0.2 ml solution (0.1 g/l) was applied to an area of a beginning labial herpes outbreak on the lip of a female. After 3-4 hours the symptoms was gone. The experiment was performed twice.

Example 7

Wound Healing Effect

Initial tests with parallel scalpel cuts through the skin including the subcutaneous tissue layer showed that wounds treated with an ointment including the active substance healed in notably shorter time compared to non-treated wounds.

The skin for the experiment was washed and disinfected with alcohol.

Wounds were created with a scalpel in a holder for uniformity and parallel cuts of 10 mm were created. Each second wound was treated with an ointment with the active substance and the other wounds were left untreated. The time for healing the non-treated wounds was on average 5 days. The treated wounds healed in clearly shorter time. The healing process was shortened, to in the best case, half the time of non-treated wounds.

Index of compounds

| Symbol | Name | Structure |
|---|---|---|
| A-01 | N²-[(benzyloxy)carbonyl]-L-arginyl-N¹-[(1S)-1-({[(2S)-2-bromo-3-phenylpropanoyl]amino}methyl)-2-methylpropyl]-L-leucinamide | 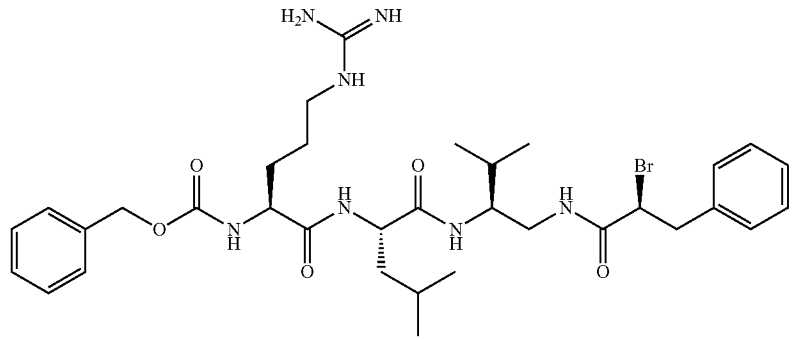 |
| A-02 | N²-[(benzyloxy)carbonyl]-L-arginyl-N¹-[(1S)-1-({[(2R)-2-bromo-3-phenylpropanoyl]amino}methyl)-2-methylpropyl]-L-leucinamide | 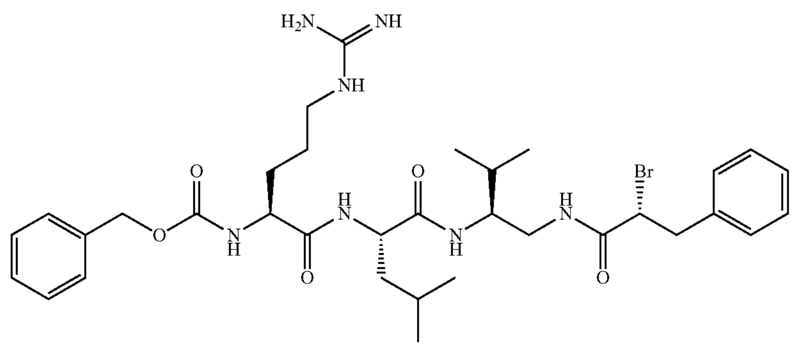 |

-continued

Index of compounds

| Symbol | Name | Structure |
|---|---|---|
| A-03 | N²-[(benzyloxy)carbonyl]-L-arginyl-N¹-[(1S)-1-({[(2S)-2-hydroxy-3-phenylpropanoyl]amino}methyl)-2-methylpropyl]-L-leucinamide | 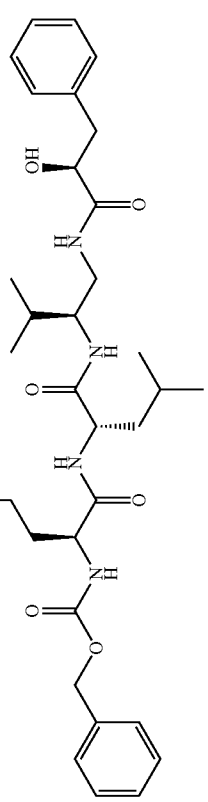 |
| A-04 | N²-[(benzyloxy)carbonyl]-L-arginyl-N¹-[(1S)-1-({[(2R)-2-hydroxy-3-phenylpropanoyl]amino}methyl)-2-methylpropyl]-L-leucinamide | 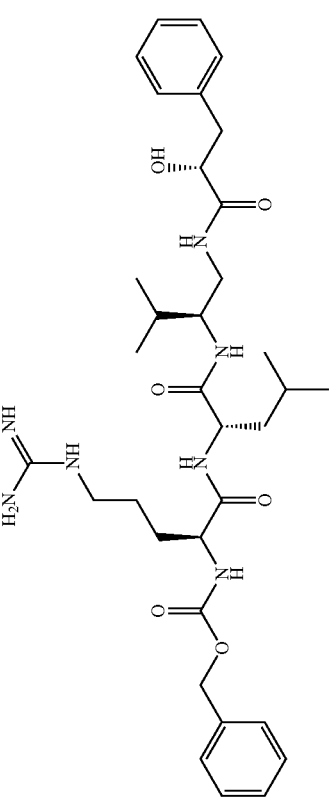 |
| A-20 | N²-[(benzyloxy)carbonyl]-L-arginyl-N¹-[(1S)-2-methyl-1-({[(2E)-3-phenylprop-2-enoyl]amino}methyl)propyl]-L-leucinamide | 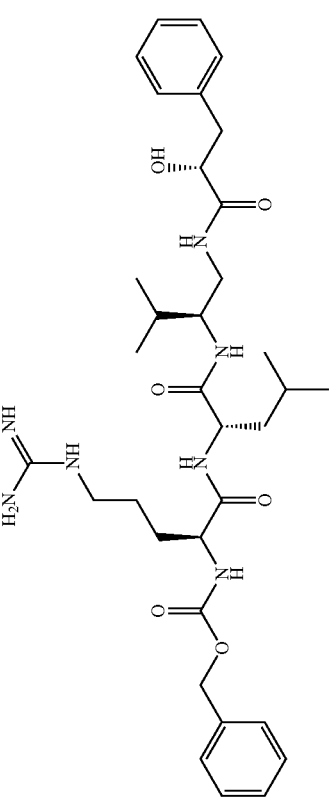 |

-continued

Index of compounds

| Symbol | Name | Structure |
|---|---|---|
| A-27 | N²-[(benzyloxy)carbonyl]-L-arginyl-N¹-[(1S)-2-methyl-1-({[(2E)-4-phenylbut-2-enoyl]amino}methyl)propyl]-L-leucinamide | 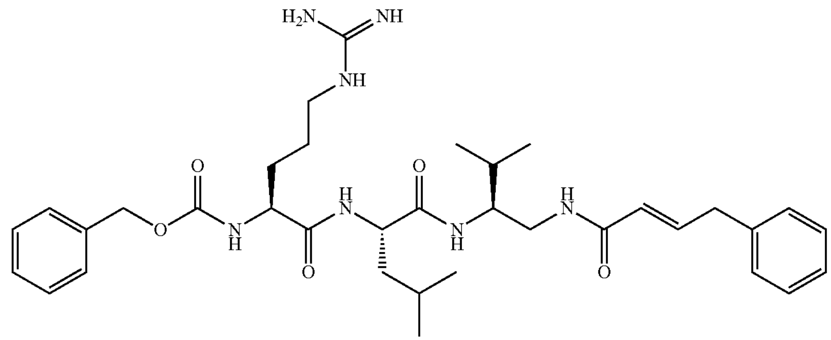 |
| A-28 | L-arginyl-N¹-[(1S)-2-methyl-1-({[(2E)-3-phenylprop-2-enoyl]amino}methyl)propyl]-L-leucinamide | 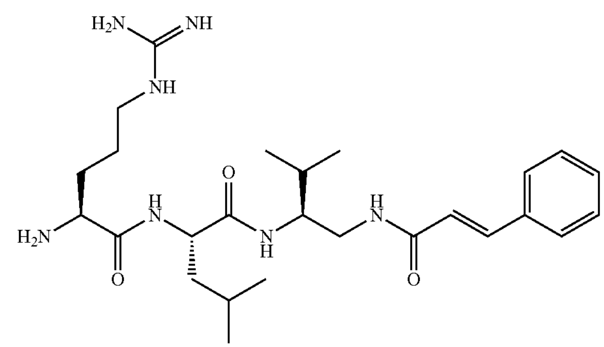 |

-continued

Index of compounds

| Symbol | Name | Structure |
|---|---|---|
| A-29 | N²-acetyl-L-arginyl-N¹-[(1S)-2-methyl-1-({[(2E)-3-phenylprop-2-enoyl]amino}methyl)propyl]-L-leucinamide | 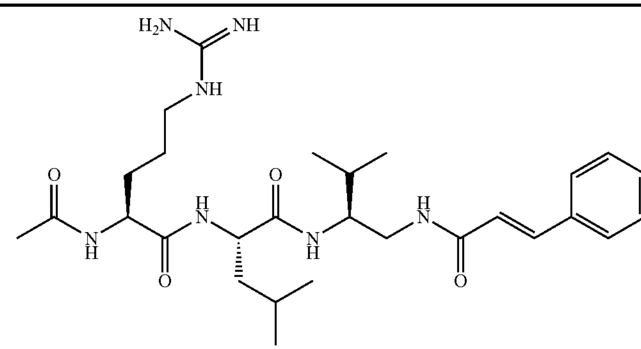 |
| A-32 I | N²-[(benzyloxy)carbonyl]-L-arginyl-N¹-{(1S)-2-methyl-1-{[(3-phenylprop-2-ynoyl)amino]methyl}aminojmethyl)aminoamide | 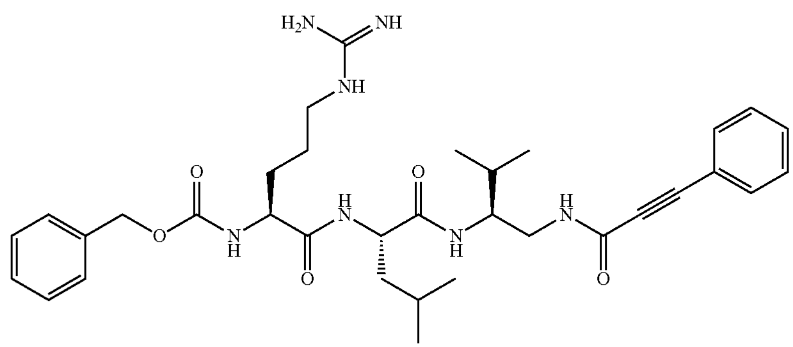 |
| A-32 II | N²-[(benzyloxy)carbonyl]-L-arginyl-N¹-{(1S)-1-({[(2Z)-2-bromo-3-phenylprop-2-enoyl]amino}methyl)-2-methylpropyl]-L-leucinamide | 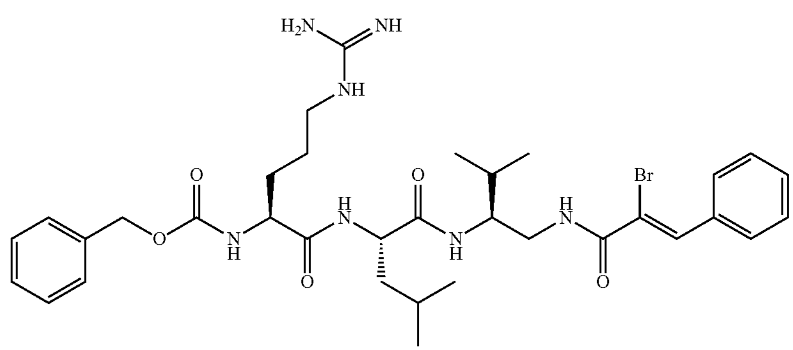 |

-continued

Index of compounds

| Symbol | Name | Structure |
|---|---|---|
| A-43 | N²-(pyridin-2-ylacetyl)-L-arginyl-N¹-[(1S)-2-methyl-1-({[(2E)-3-phenylprop-2-enoyl]amino}methyl)propyl]-L-leucinamide | 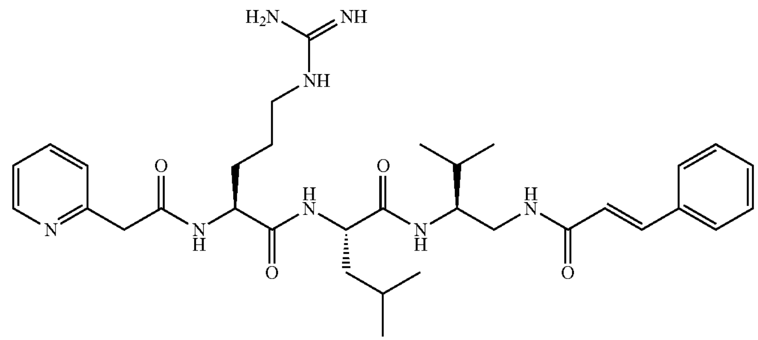 |
| A-45 | N²-(pyridin-4-ylacetyl)-L-arginyl-N¹-[(1S)-2-methyl-1-({[(2E)-3-phenylprop-2-enoyl]amino}methyl)propyl]-L-leucinamide | 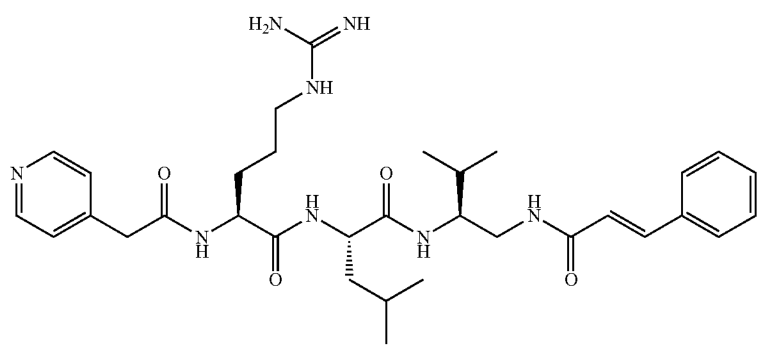 |

-continued
Index of compounds
| Symbol | Name | Structure |
|---|---|---|
| A-49 | N²-[(benzyloxy)carbonyl]-L-arginyl-N¹-[(1S)-2-methyl-1-({[(2E)-3-pyridin-4-ylprop-2-enoyl]amino}methyl)propyl]-L-leucinamide | 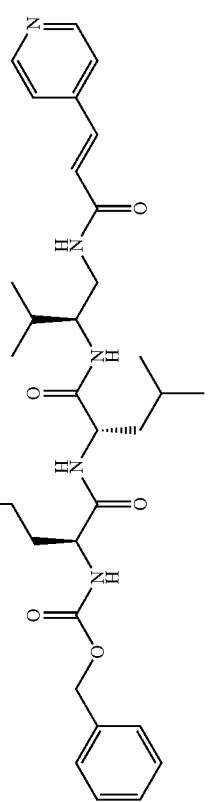 |
| A-56 | N²-[(benzyloxy)carbonyl]-L-arginyl-L-leucyl-N¹-[(1S)-2-amino-2-oxo-1-phenylethyl]-L-valinamide | 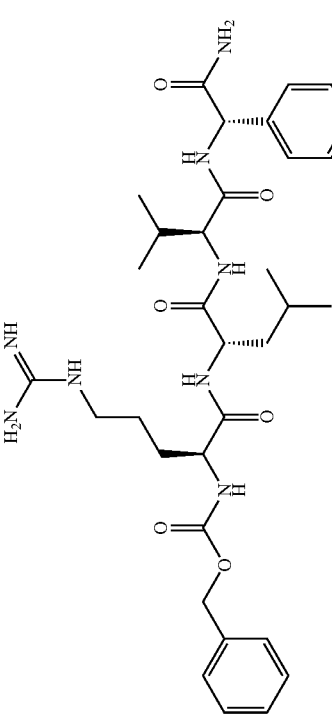 |

-continued

Index of compounds

| Symbol | Name | Structure |
|---|---|---|
| A-57 | N²-(phenylacetyl)-L-arginyl-L-leucyl-N¹-[(1S)-2-amino-2-oxo-1-phenylethyl]-L-valinamide | 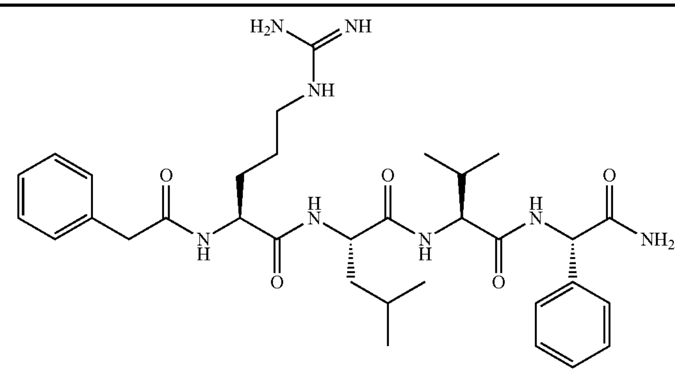 |
| A-58 | N²-(4-phenylbutanoyl)-L-arginyl-L-leucyl-N¹-[(1S)-2-amino-2-oxo-1-phenylethyl]-L-valinamide | 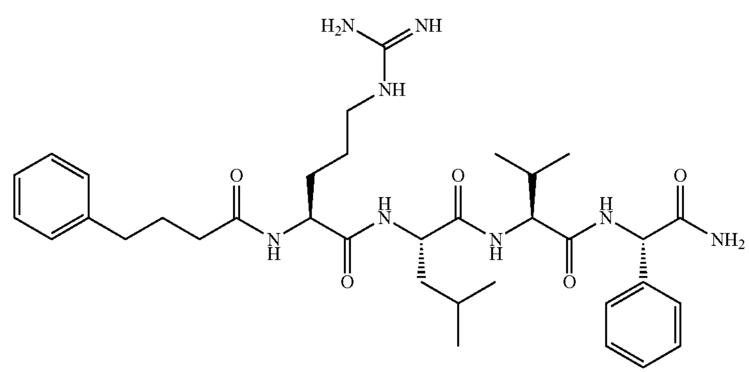 |

-continued

Index of compounds

| Symbol | Name | Structure |
|---|---|---|
| A-59 | N²-(3-phenylpropanoyl)-L-arginyl-L-leucyl-N¹-[(1S)-2-amino-2-oxo-1-phenylethyl]-L-valinamide | 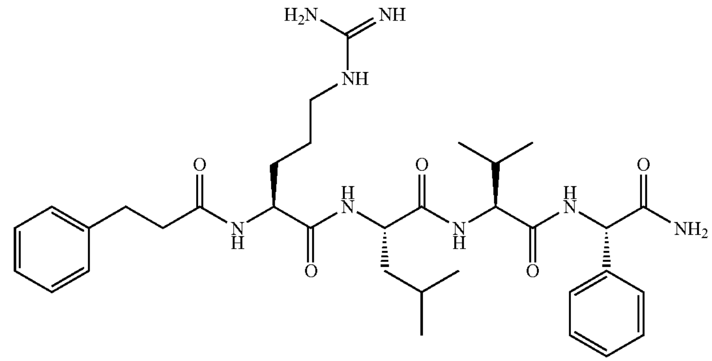 |
| A-60 | N²-[(benzyloxy)carbonyl]-L-arginyl-N¹-((1S)-2-methyl-1-{[(phenylacetyl)amino]methyl}propyl)-L-leucinamide | 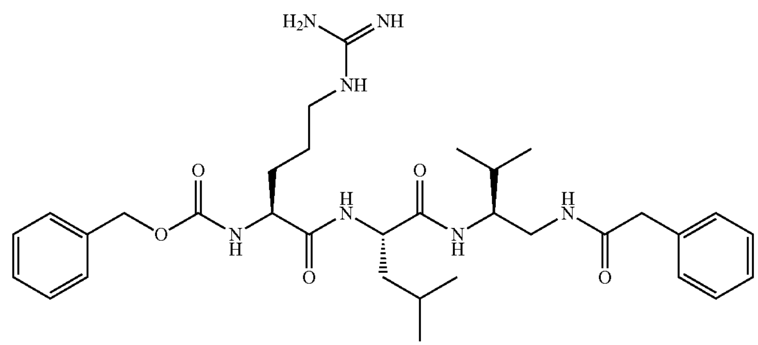 |

-continued
Index of compounds
| Symbol | Name | Structure |
|---|---|---|
| A-61 | N²-[(benzyloxy)carbonyl]-L-arginyl-N¹-((1S)-2-methyl-1-{[(3-phenylpropanoyl)amino]methyl}propyl)-L-leucinamide | 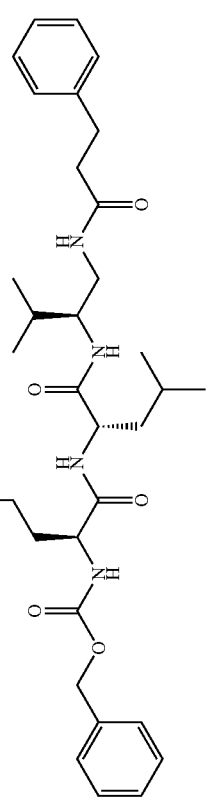 |
| A-62 | N²-[(benzyloxy)carbonyl]-L-arginyl-N¹-((1S)-2-methyl-1-{[(4-phenylbutanoyl)amino]methyl}propyl)-L-leucinamide | 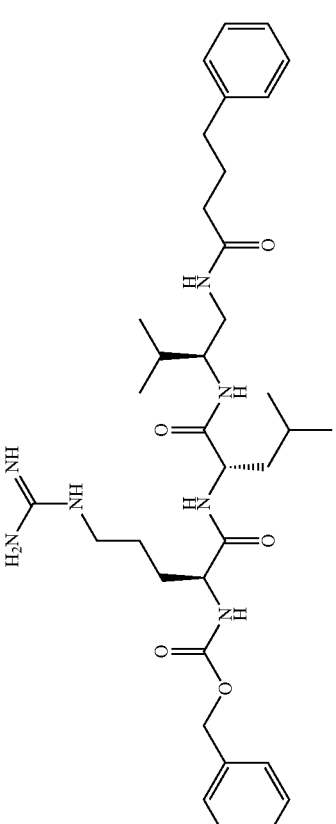 |

-continued

Index of compounds

| Symbol | Name | Structure |
|---|---|---|
| A-63 | N²-[(2E)-3-phenylprop-2-enoyl]-L-arginyl-L-leucyl-N¹-[(1S)-2-amino-2-oxo-1-phenylethyl]-L-valinamide | 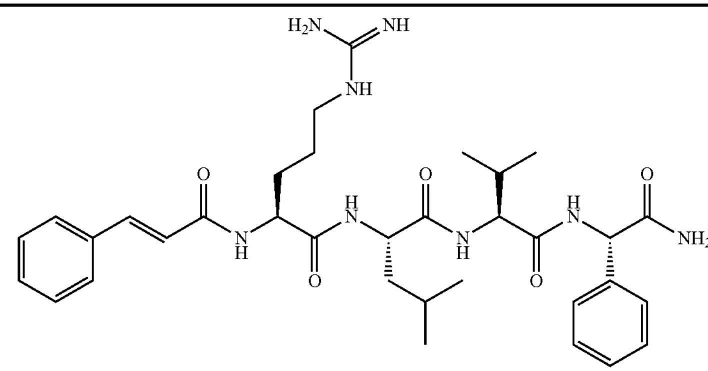 |
| A-64 | N²-(phenylacetyl)-L-arginyl-N¹-({[(2E)-3-phenylprop-2-enoyl]amino}methyl)propyl]-L-leucinamide | 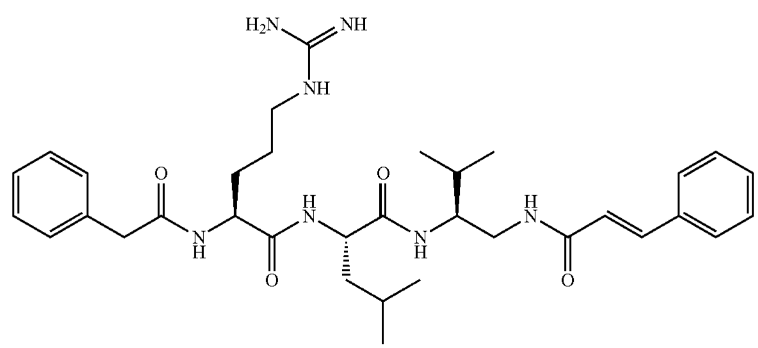 |

-continued

Index of compounds

| Symbol | Name | Structure |
|---|---|---|
| A-65 | N²-(3-phenylpropanoyl)-L-arginyl-N¹-[(1S)-2-methyl-1-({[(2E)-3-phenylprop-2-enoyl]amino}methyl)propyl]-L-leucinamide | 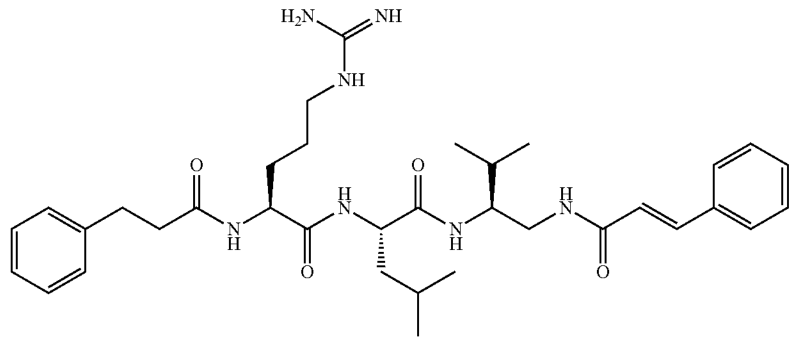 |
| A-66 | N²-(4-phenylbutanoyl)-L-arginyl-N¹-[(1S)-2-methyl-1-({[(2E)-3-phenylprop-2-enoyl]amino}methyl)propyl]-L-leucinamide | 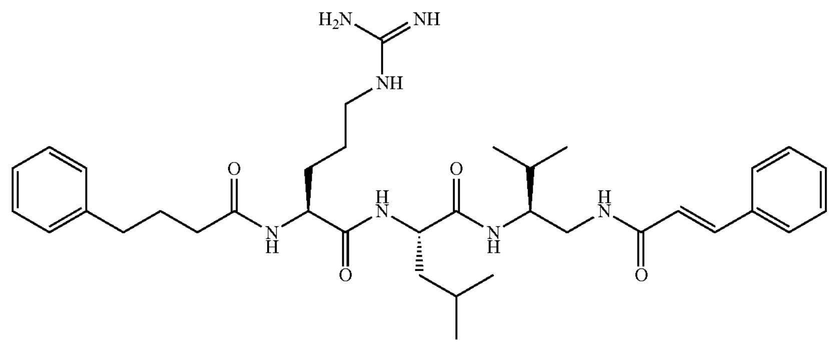 |
| A-67 | N²-[(benzyloxy)carbonyl]-L-arginyl-L-leucyl-N¹-[(2E)-3-phenylprop-2-enyl]-L-valinamide | 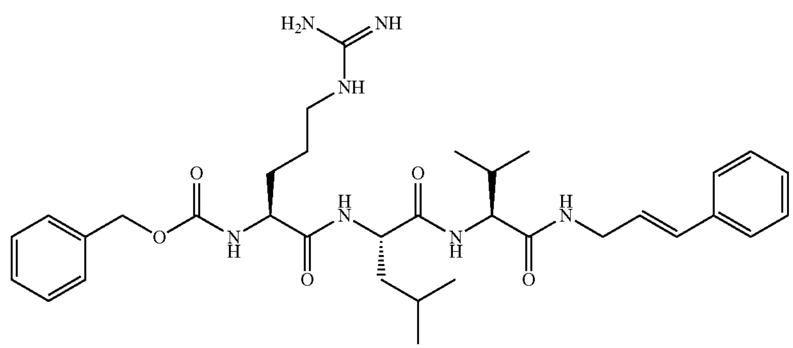 |

-continued

Index of compounds

| Symbol | Name | Structure |
|---|---|---|
| A-68 | N²-[(2S)-2-(acetylamino)-2-phenylethanoyl]-L-arginyl-L-leucyl-N¹-[(1S)-2-amino-2-oxo-1-phenylethyl]-L-valinamide | 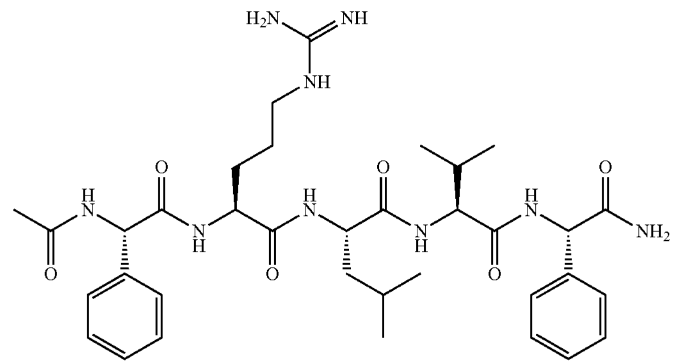 |
| A-71 | N²-[(benzyloxy)carbonyl]-L-arginyl-N¹-((1S)-2-methyl-1-{[(6-phenylhexanoyl)amino]methyl}propyl)-L-leucinamide | 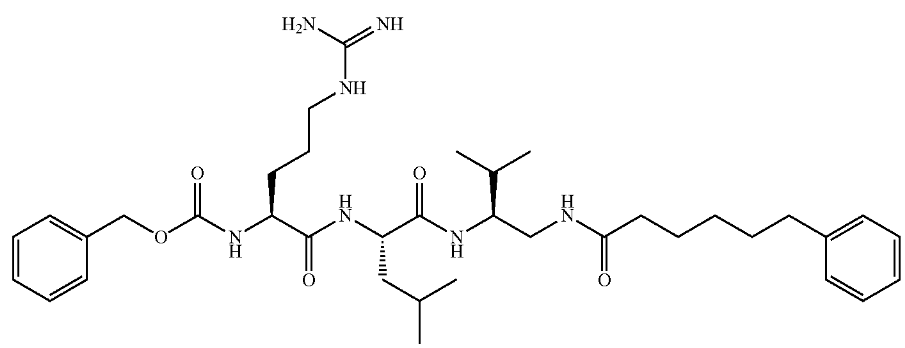 |

-continued
Index of compounds
| Symbol | Name | Structure |
|---|---|---|
| A-72 | N²-[(benzyloxy)carbonyl]-L-arginyl-N¹-(((1S)-2-methyl-1-{[(5-phenylpentanoyl)amino]methyl}propyl)-L-leucinamide | 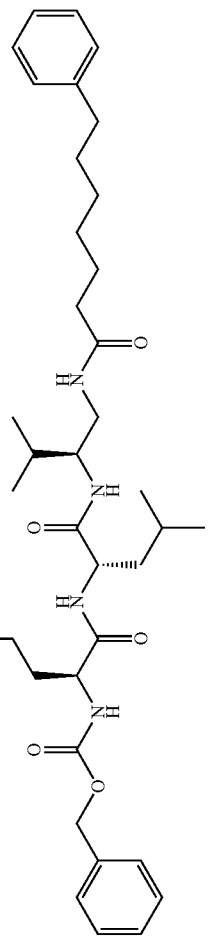 |
| A-73 | N²-[(benzyloxy)carbonyl]-L-arginyl-N¹-(((1S)-2-methyl-1-{[(7-phenylheptanoyl)amino]methyl}propyl)-L-leucinamide | 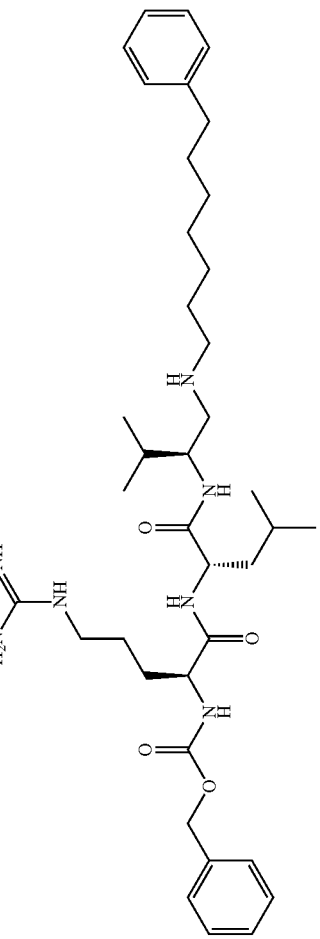 |
| A-74 | N²-[(benzyloxy)carbonyl]-L-arginyl-N¹-{[(1S)-2-methyl-1-({[(2E,4E)-5-phenylpenta-2,4-dienoyl]amino}methyl)propyl]-L-leucinamide | 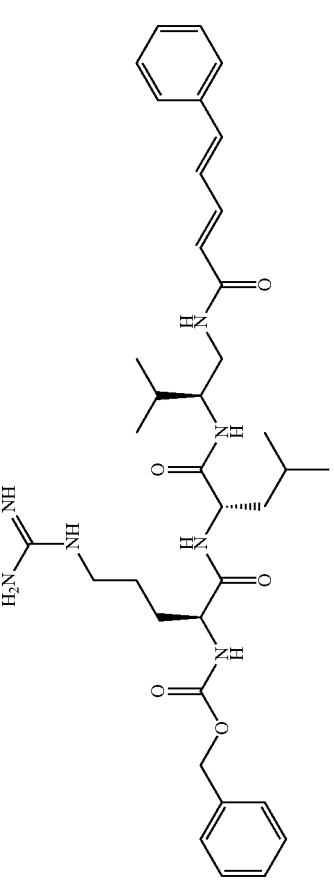 |

-continued

Index of compounds

| Symbol | Name | Structure |
|---|---|---|
| A-75 | N²-[(benzyloxy)carbonyl]-L-arginyl-N¹-[(1S)-1-({[(2E)-3-(1,1'-biphenyl-4-yl)prop-2-enoyl]amino}methyl)-2-methylpropyl]-L-leucinamide | 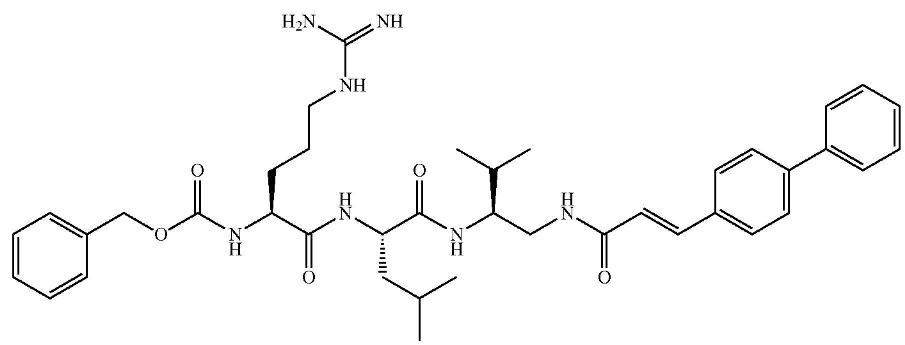 |
| A-76 | N²-[(benzyloxy)carbonyl]-L-arginyl-N¹-((1S)-2-methyl-1-{[(8-phenyloctanoyl)amino]methyl}propyl)-L-leucinamide | 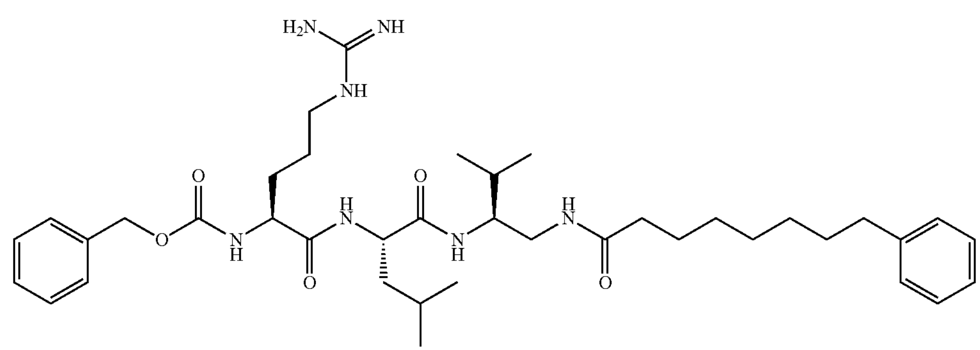 |

-continued

Index of compounds

| Symbol | Name | Structure |
|---|---|---|
| A-79 | N²-[(benzyloxy)carbonyl]-L-arginyl-(2S)-N¹-((3S)-1-benzyl-1-{N²-[(benzyloxy)carbonyl]-L-arginyl-L-leucyl]-5-oxopiperazin-2-yl)-N-((5S)-5-benzyl-1-{N²-[(benzyloxy)carbonyl]-L-arginyl-L-leucyl}-3-oxopiperazin-2-yl)-L-leucinamide | 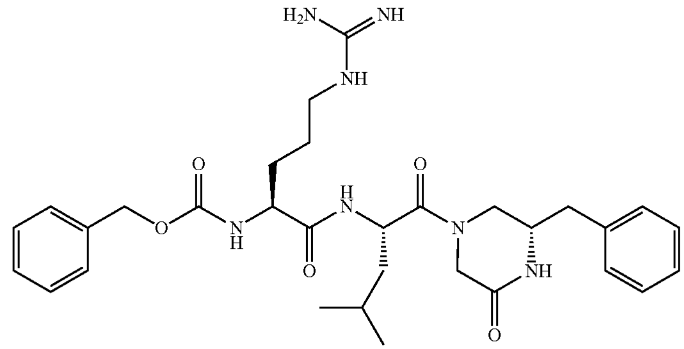 |
| A-83 | N²-[(benzyloxy)carbonyl]-L-arginyl-N¹-((1S)-1-benzyl-2-{[(2E)-3-phenylprop-2-enoyl]amino}ethyl)-L-leucinamide | 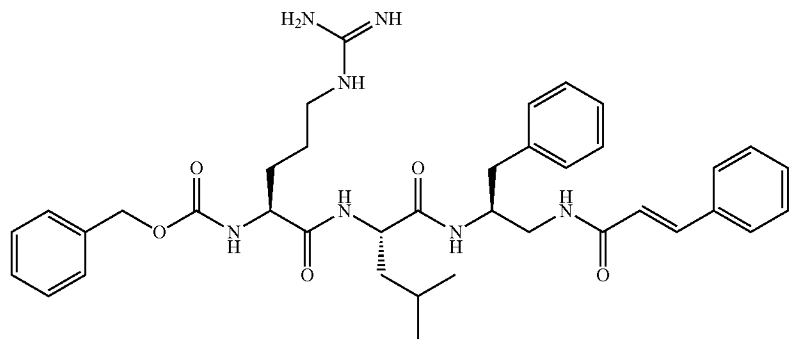 |
| A-84 | N²-[(benzyloxy)carbonyl]-L-arginyl-N¹-[(1S)-3-methyl-1-({[(2E)-3-phenylprop-2-enoyl]amino}methyl)butyl]-L-leucinamide | 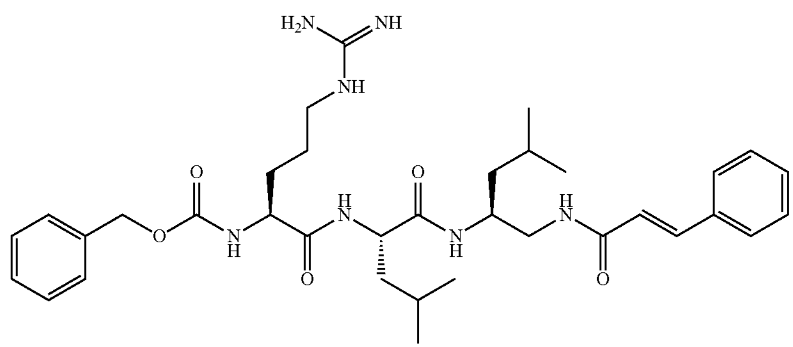 |

-continued

Index of compounds

| Symbol | Name | Structure |
|---|---|---|
| A-85 | N²-[(benzyloxy)carbonyl]-D-arginyl-N¹-[(1S)-2-methyl-1-({[(2E)-3-phenylprop-2-enoyl]amino}methyl)propyl]-L-leucinamide | 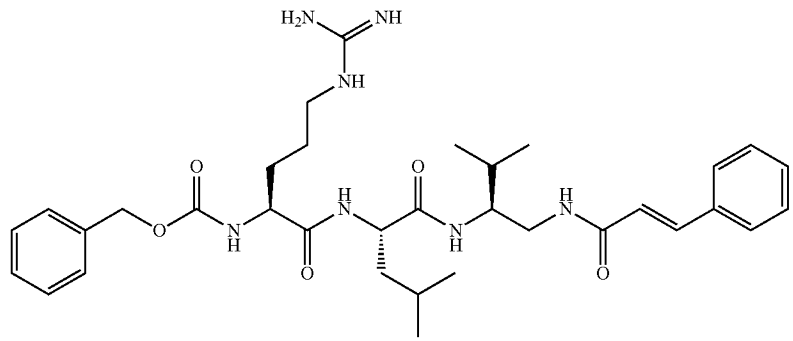 |
| A-86 | N²-[(benzyloxy)carbonyl]-L-arginyl-N¹-[(1S)-2-methyl-1-({[(2E)-3-phenylprop-2-enoyl]amino}methyl)propyl]-D-leucinamide | 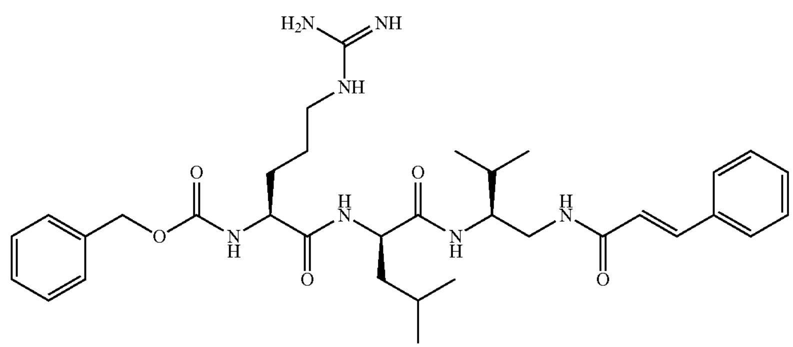 |

-continued

Index of compounds

| Symbol | Name | Structure |
|---|---|---|
| A-87 | N²-[(benzyloxy)carbonyl]-L-arginyl-N¹-[(1R)-2-methyl-1-({[(2E)-3-phenylprop-2-enoyl]amino}methyl)propyl]-L-leucinamide | 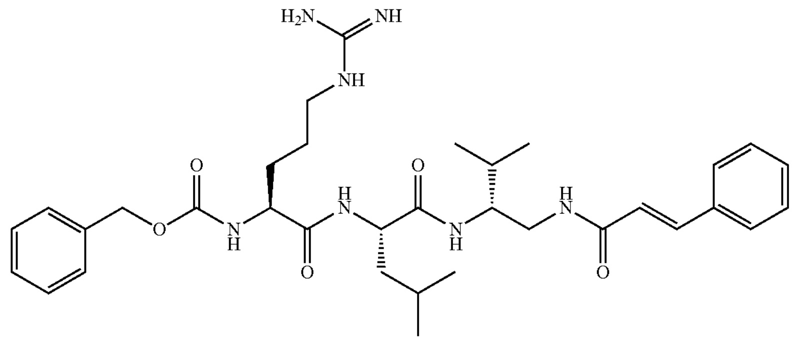 |
| A-88 | N²-[(benzyloxy)carbonyl]-L-arginyl-N¹-{(2S)-3-methyl-2-[3-phenylpropanoyl)amino]butyl}-L-leucinamide | 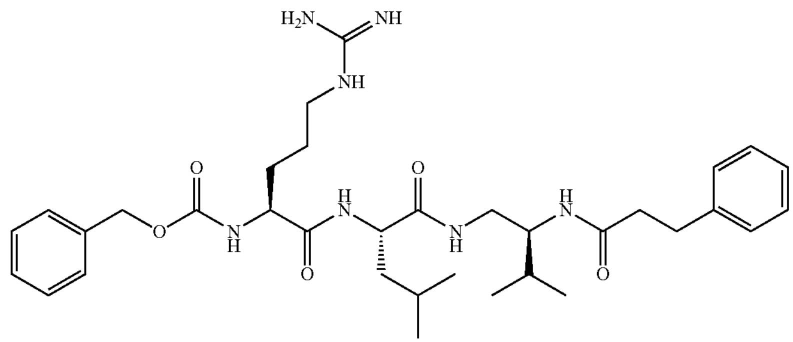 |
| A-89 | N²-[(benzyloxy)carbonyl]-L-arginyl-N-[(1S)-2-methyl-1-({[(2E)-3-phenylprop-2-enoyl]amino}methyl)propyl]-L-prolinamide | 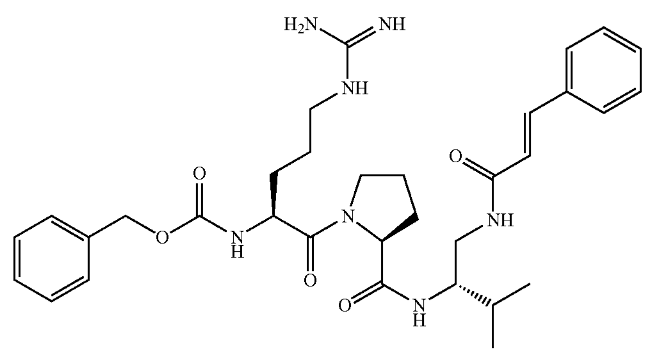 |

-continued
Index of compounds
| Symbol | Name | Structure |
|---|---|---|
| A-90 | N²-[(benzyloxy)carbonyl]-L-arginyl-N-[(1S)-2-methyl-1-({[(2E)-3-phenylprop-2-enoyl]amino}methyl)propyl]-L-phenylalaninamide | 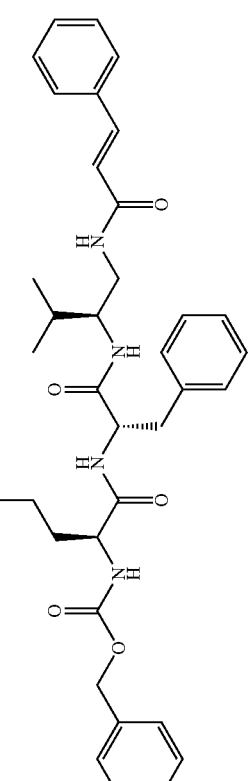 |
| A-91 | N²-[(benzyloxy)carbonyl]-L-arginyl-N¹-[(1S)-2-methyl-1-({[(2E)-3-phenylprop-2-enoyl]amino}methyl)propyl]-L-serinamide | 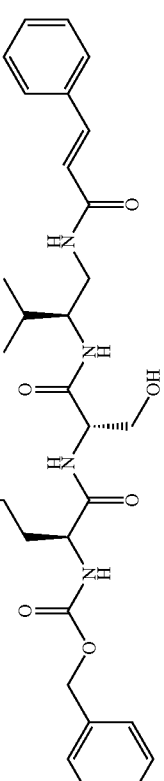 |
| A-92 | N²-[(benzyloxy)carbonyl]-L-arginyl-N¹-[(1S)-2-methyl-1-({[(2E)-3-phenylprop-2-enoyl]amino}methyl)propyl]glycinamide | 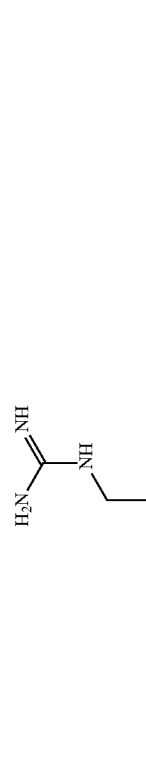 |

-continued

Index of compounds

| Symbol | Name | Structure |
|---|---|---|
| A-93 | N²-[(benzyloxy)carbonyl]-L-arginyl-N¹-[(1S)-2-methyl-1-({[(2E)-3-phenylprop-2-enoyl]amino}methyl)propyl]-L-threoninamide | 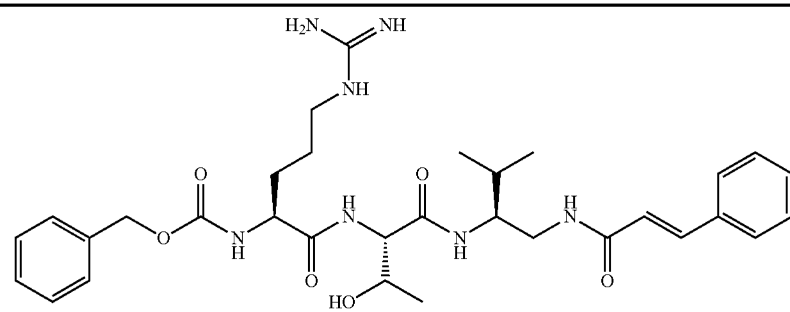 |
| A-94 | N²-[(benzyloxy)carbonyl]-L-arginyl-N¹-(2-{[(2E)-3-phenylprop-2-enoyl]amino}ethyl)-L-leucinamide | 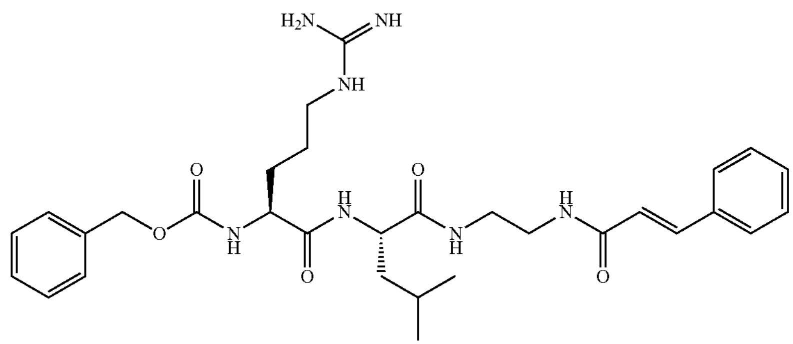 |
| A-95 | N²-[(benzyloxy)carbonyl]-L-arginyl-N¹-[(1R,2R)-2-hydroxy-1-({[(2E)-3-phenylprop-2-enoyl]amino}methyl)propyl]-L-leucinamide | 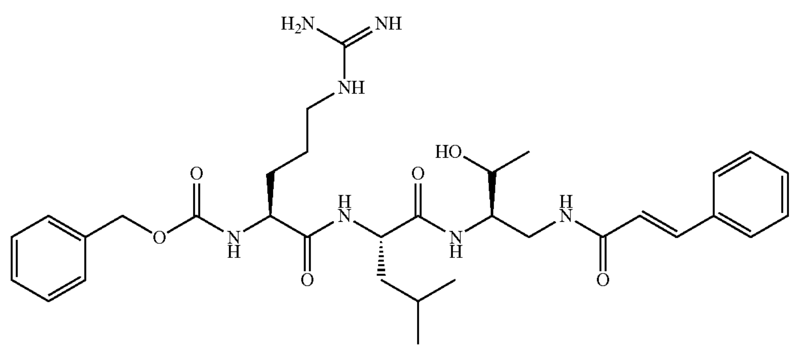 |

-continued

Index of compounds

| Symbol | Name | Structure |
|---|---|---|
| A-96 | N²-[(benzyloxy)carbonyl]-L-arginyl-N²-methyl-N¹-[(1S)-2-methyl-1-({[(2E)-3-phenylprop-2-enoyl]amino}methyl)propyl]glycinamide | 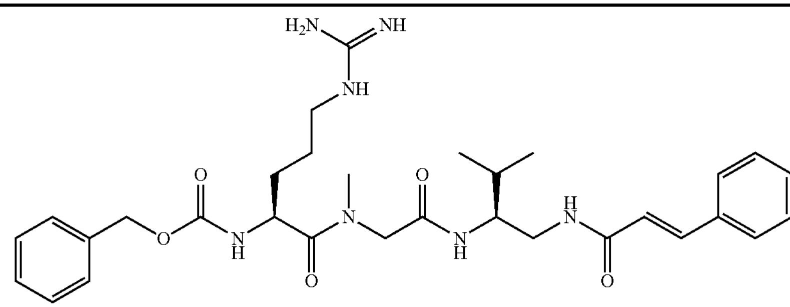 |
| A-97 | N²-[(benzyloxy)carbonyl]-L-arginyl-N¹-((2S)-3-methyl-2-{[(2E)-3-phenylprop-2-enoyl]amino}butyl)-L-leucinamide | 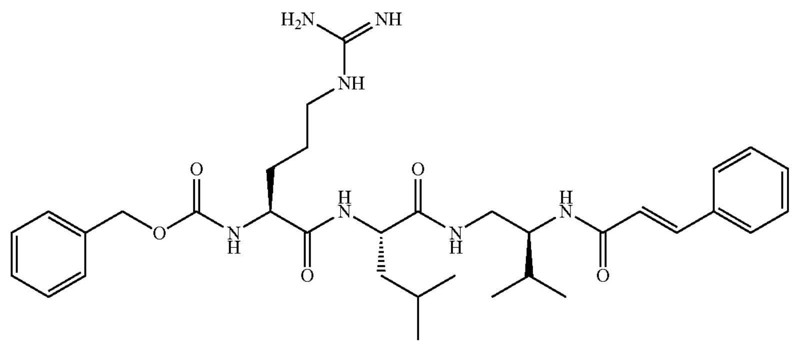 |
| A-109 | N²-[(benzyloxy)carbonyl]-L-arginyl-N¹-((1S)-1-methyl-2-{[(2E)-3-phenylprop-2-enoyl]amino}ethyl)-L-leucinamide | 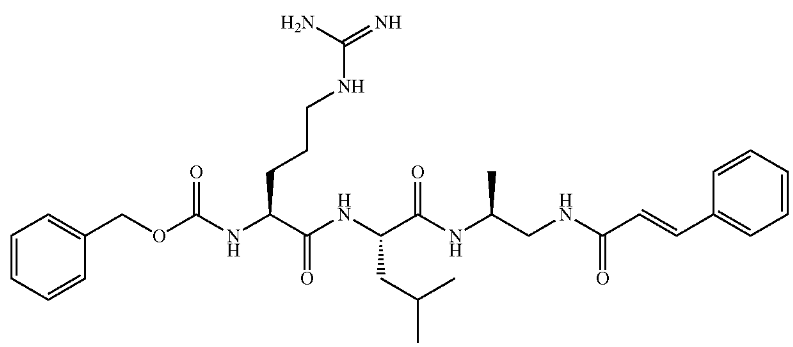 |

-continued
Index of compounds
| Symbol | Name | Structure |
|---|---|---|
| A-110 | N²-[(benzyloxy)carbonyl]-L-arginyl-N¹-{(1S)-1-[({N-[((7-hydroxy-2-oxo-2H-chromen-3-yl)acetyl]-L-phenylalanyl}amino)methyl]-2-methylpropyl}-L-leucinamide | 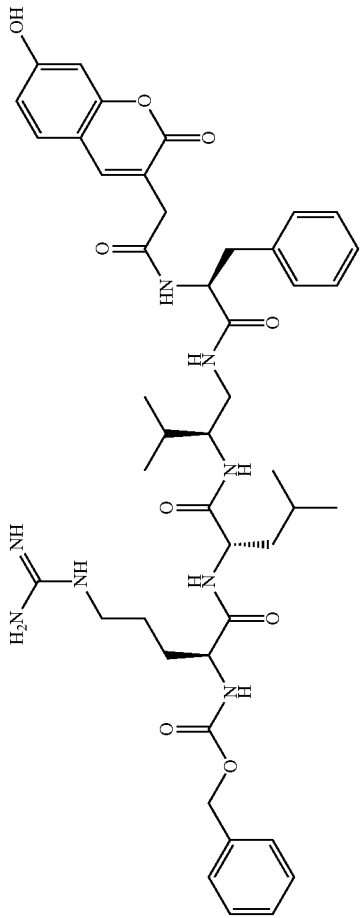 |
| A-111 | N-[((7-hydroxy-2-oxo-2H-chromen-3-yl)acetyl]glycyl-N-[(2S)-2-({N²-[(benzyloxy)carbonyl]-L-arginyl-L-leucyl}amino)-3-methylbutyl]-L-phenylalaninamide | 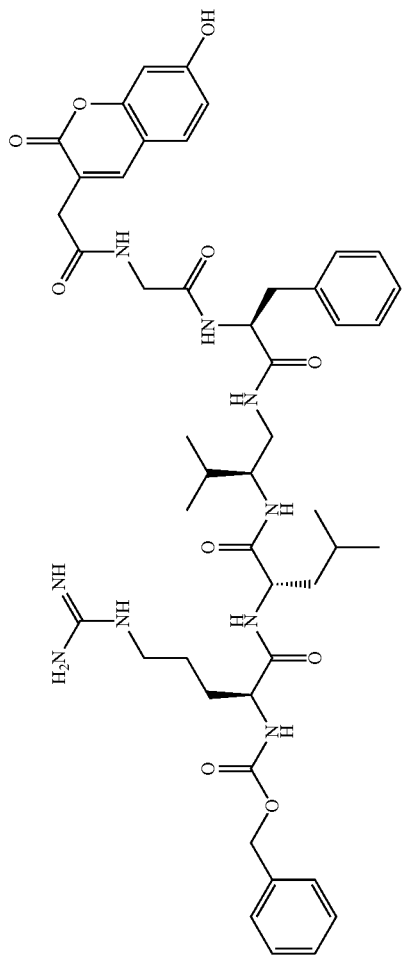 |

-continued

Index of compounds

| Symbol | Name | Structure |
|---|---|---|
| A-112 | N-acetylglycyl-N-[(2S)-2-({N²-[(benzyloxy)carbonyl]-L-arginyl-L-leucyl}amino)-3-methylbutyl]-L-phenylalaninamide | 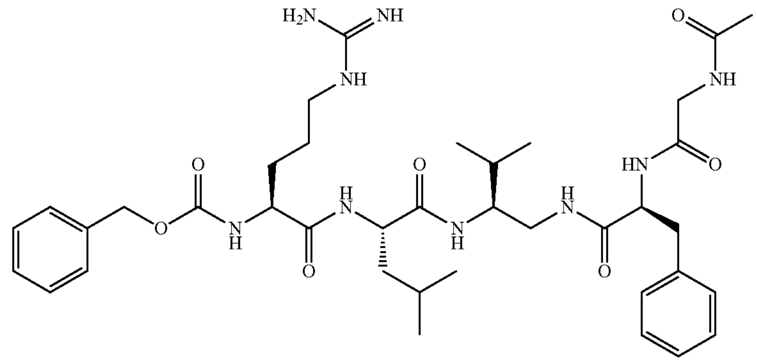 |
| A-129 | N-acetylglycyl-N-[(2S)-2-({N²-[(benzyloxy)carbonyl]-L-arginyl-L-leucyl}amino)-3-methylbutyl]-D-phenylalaninamide | 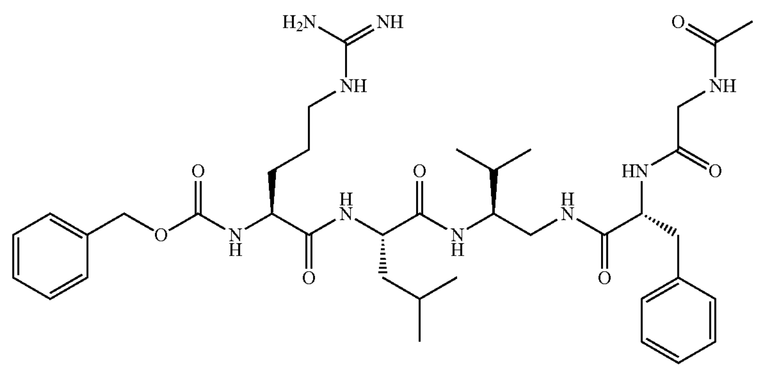 |

-continued

Index of compounds

| Symbol | Name | Structure |
|---|---|---|
| A-130 | N²-[(benzyloxy)carbonyl]-L-arginyl-L-leucyl-N¹-[(1S)-2-amino-2-oxo-1-phenylethyl]-N²-isopropylglycinamide | (structure) |
| A-131 | N²-[(benzyloxy)carbonyl]-L-arginyl-N²-methyl-N¹-[(1S)-2-methyl-1-({[(2E)-3-phenylprop-2-enoyl]amino}methyl)propyl]-L-leucinamide | (structure) |

-continued

Index of compounds

| Symbol | Name | Structure |
|---|---|---|
| A-132 | N²-[(benzyloxy)carbonyl]-L-arginyl-N¹-((1S)-1-{[(N-acetyl-L-phenylalanyl)amino]methyl}-2-methylpropyl)-L-leucinamide | 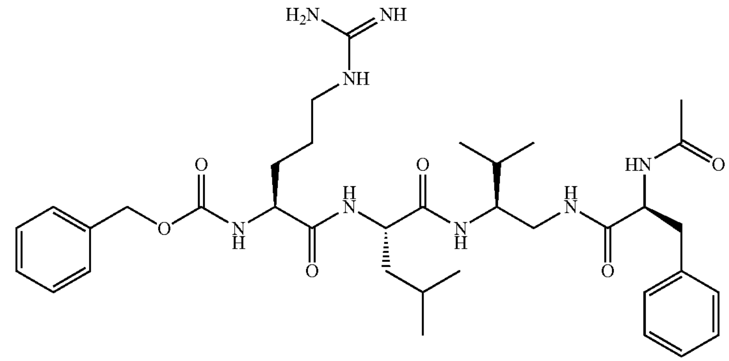 |
| A-133 | N²-[(benzyloxy)carbonyl]-L-arginyl-N¹-((1S)-1-{[(N-acetyl-D-phenylalanyl)amino]methyl}-2-methylpropyl)-L-leucinamide | 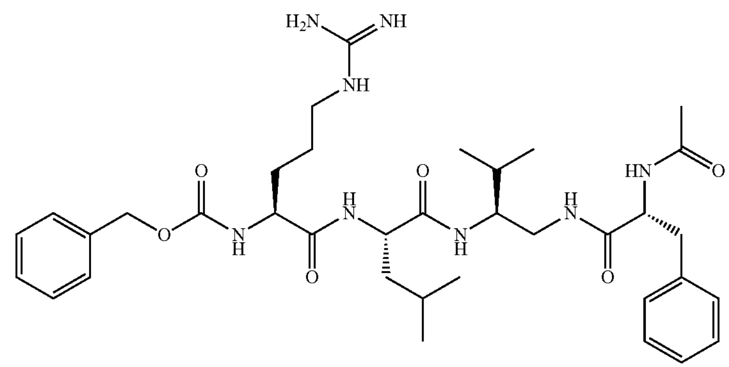 |

The invention claimed is:

1. A compound selected from the group consisting of:
   (a) $N^2$-[(benzyloxy)carbonyl]-D/L-arginyl-$N^1$-[(1S)-2-methyl-1-({[(2E)-4-phenylbut-2-enoyl]amino}methyl)propyl]-D/L-leucinamide;
   (b) $N^2$-[(benzyloxy)carbonyl]-L-arginyl-$N^1$-((1S)-1-({[(2Z)-2-bromo-3-phenylprop-2-enoyl]amino}methyl)-2-methylpropyl]-D/L-leucinamide;
   (c) $N^2$-(3-phenylpropanoyl)-D/L-arginyl-$N^1$-[(1S)-2-methyl-1-({[(2E)-3-phenylprop-2-enoyl]amino}methyl)propyl]-D/L-leucinamide;
   (d) $N^2$-[(benzyloxy)carbonyl]-D/L-arginyl-$N^1$-((1S)-2-methyl-1-{[(6-phenylhexanoyl)amino]methyl}propyl)-D/L-leucinamide; and
   (e) $N^2$-[(benzyloxy)carbonyl]-D/L-arginyl-$N^1$-[(1S)-2-methyl-1-({[(2E,4E)-5-phenylpenta-2,4-dienoyl]amino}methyl)propyl]-D/L-leucinamide,
   wherein each D/L independently represents D or L.

2. The compound according to claim 1, wherein the compound is $N^2$-[(benzyloxy)carbonyl]-D/L-arginyl-$N^1$-[(1S)-2-methyl-1-({[(2E)-4-phenylbut-2-enoyl]amino}methyl)propyl]-D/L-leucinamide.

3. The compound according to claim 1, wherein the compound is $N^2$-[(benzyloxy)carbonyl]-L-arginyl-$N^1$-[(1S)-2-methyl-1-({[(2E)-4-phenylbut-2-enoyl]amino}methyl)propyl]-L-leucinamide.

4. A pharmaceutical composition comprising the compound according to claim 1 and a pharmaceutically acceptable diluent, adjuvant, carrier, excipient or buffer.

5. A pharmaceutical composition comprising the compound according to claim 2 and a pharmaceutically acceptable diluent, adjuvant, carrier, excipient or buffer.

6. A pharmaceutical composition comprising the compound according to claim 3 and a pharmaceutically acceptable diluent, adjuvant, carrier, excipient or buffer.

7. A method of treating a patient comprising: administering to a patient having a microbial disease or infection a compound of any of claims 1-3, wherein the microorganism is selected from the group consisting of bacteria and virus, wherein the bacteria is selected from the group consisting of Staphylococci, Pneumococci, Streptococci and Listeria, and wherein the virus is selected from the group consisting of polio viruses, Herpesviridae, hepatitis B and HSV-1.

* * * * *